US012230400B2

(12) United States Patent
McNair

(10) Patent No.: US 12,230,400 B2
(45) Date of Patent: *Feb. 18, 2025

(54) DETERMINING A CARDIOVASCULAR ISCHEMIC EVENT AND DECISION SUPPORT TOOL

(71) Applicant: Cerner Innovation, Inc., Kansas City, MO (US)

(72) Inventor: Douglas S. McNair, Leawood, KS (US)

(73) Assignee: Cerner Innovation, Inc., Kansas City, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/429,058

(22) Filed: Jan. 31, 2024

(65) Prior Publication Data

US 2024/0170148 A1   May 23, 2024

Related U.S. Application Data

(63) Continuation of application No. 16/141,682, filed on Sep. 25, 2018, now Pat. No. 11,942,219.
(Continued)

(51) Int. Cl.
*G16H 50/20* (2018.01)
*G01N 33/68* (2006.01)
(Continued)

(52) U.S. Cl.
CPC ......... *G16H 50/20* (2018.01); *G01N 33/6893* (2013.01); *G16H 40/63* (2018.01);
(Continued)

(58) Field of Classification Search
USPC ........................................... 705/2–3
See application file for complete search history.

(56) References Cited

U.S. PATENT DOCUMENTS

| 11,942,219 B1 * | 3/2024 | McNair ............... G16H 50/30 |
| 2004/0122707 A1 | 6/2004 | Sabol et al. |

(Continued)

OTHER PUBLICATIONS

Renuji, B. (2017). A study of serum uric acid and C-reactive protein levels in metabolic syndrome subjects with and . . . in a tertiary care hospital (Order No. 30276218). Available from ProQuest Dissertations and Theses Professional. (2786887447). Retrieved from https://dialog.proquest.co (Year: 2017).*

(Continued)

*Primary Examiner* — Christopher L Gilligan
*Assistant Examiner* — Bennett Stephen Erickson
(74) *Attorney, Agent, or Firm* — Invoke

(57) ABSTRACT

Decision support technology is provided for use with patients who may be prone to a cardiovascular condition such as acute coronary syndromes. A mechanism is provided to determine a patient's risk for experiencing a cardiovascular ischemic event at a future time interval based on temporal patterns determined using physiological parameters of the patient such as serum or blood uric acid and/or C-reactive protein (CRP). A forecast or score may be determined indicating whether or not temporal patterns merit intervention to prevent occurrence or reoccurrence of ischemic events, or for determining adherence to or efficacy of treatment or preventive interventions. Based on the forecast or score, appropriate response action such as automatically issuing an alert or notification to a caregiver associated with the patient, may be determined, recommended, or implemented.

20 Claims, 17 Drawing Sheets

Related U.S. Application Data

(60) Provisional application No. 62/562,761, filed on Sep. 25, 2017.

(51) Int. Cl.
 G16H 10/60 (2018.01)
 G16H 40/63 (2018.01)

(52) U.S. Cl.
 CPC . *G01N 2333/4737* (2013.01); *G01N 2800/32* (2013.01); *G01N 2800/52* (2013.01); *G16H 10/60* (2018.01)

(56) References Cited

U.S. PATENT DOCUMENTS

| | | | |
|---|---|---|---|
| 2010/0274756 A1* | 10/2010 | Inokuchi | G16Z 99/00 707/E17.054 |
| 2014/0073861 A1* | 3/2014 | Rodriguez-Llorente | A61B 5/7264 600/301 |
| 2014/0088072 A1 | 3/2014 | Asztalos et al. | |
| 2014/0187519 A1* | 7/2014 | Cooke | G01N 33/6893 514/263.36 |
| 2014/0257852 A1 | 9/2014 | Walker et al. | |
| 2014/0296089 A1 | 10/2014 | Holmes et al. | |
| 2014/0358585 A1* | 12/2014 | Reiner | G06F 16/219 705/3 |
| 2015/0066533 A1* | 3/2015 | Lynn | G16H 50/70 705/2 |
| 2015/0185239 A1 | 7/2015 | Tsimikas et al. | |
| 2016/0069919 A1* | 3/2016 | Holmes | G01N 21/51 435/14 |
| 2016/0143594 A1* | 5/2016 | Moorman | A61B 5/7246 705/2 |
| 2016/0169911 A1* | 6/2016 | Block | G01N 33/6869 422/69 |
| 2016/0334419 A1 | 11/2016 | Block et al. | |
| 2019/0216350 A1* | 7/2019 | Sullivan | A61B 7/00 |

OTHER PUBLICATIONS

Brady, T. M. (2014). Pediatric hypertension—insights into etiology, diagnosis and progression of target organ damage (Order No. 10302160). Available from ProQuest Dissertations and Theses Professional. (1859082515) (Year: 2014).

* cited by examiner

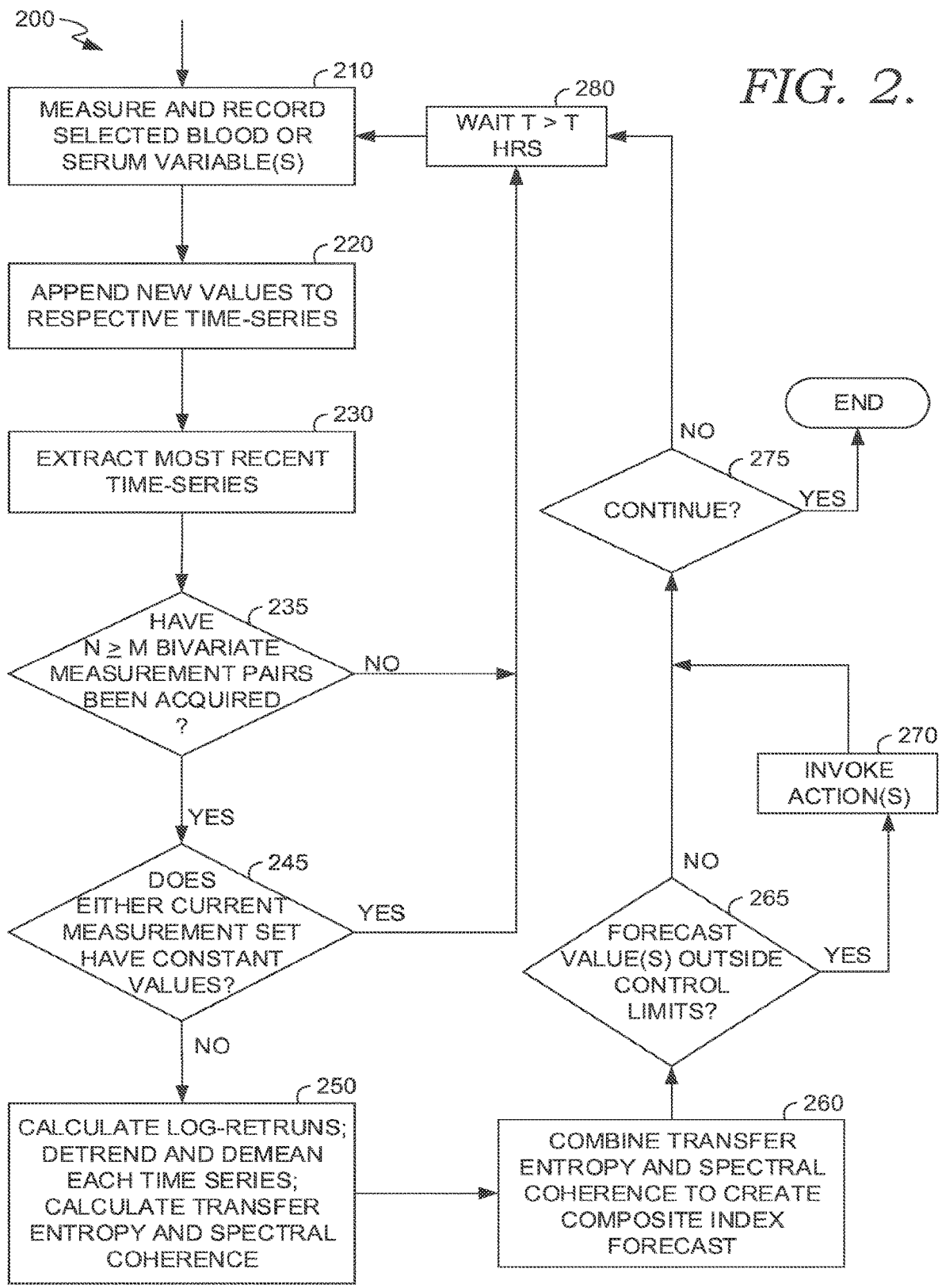

```
##############################################################################

#   TRANSFER ENTROPY AND COHERENCE OF DAILY URIC ACID AND HSCRP TIME SERIES LOG
RETURNS

#      normal = weak or no bivariate coherence plus weak or no evidence of hsCRP dependence on
uric
#      high CAD event risk = strong bivariate coherence plus strong evidence of hsCRP dependence

######################################################################## library(mvLSW)
library(seewave)
library(TransferEntropy)

# function defs
ccoh_u_c <- function (uric, hsCRP, f, wl = 32, ovlp = 0, plot = TRUE, grid = TRUE,
    scale = TRUE, cont = FALSE, collevels = seq(0, 1, 0.01),
    palette = reverse.heat.colors, contlevels = seq(0, 1, 0.01),
    colcont = "black", colbg = "white", colgrid = "black", colaxis = "black",
    collab = "black", xlab = "Rescaled Time (0-1 = 0-32 days)", ylab = "Frequency [day]^-1",
    scalelab = "Coherence", main = NULL, scalefontlab = 1, scalecexlab = 0.75,
    axisX = TRUE, axisY = TRUE, flim = NULL, flimd = NULL, ...)
{
    input1 <- inputw(wave = cbind(uric), f = f)
    uric <- input1$w
    f <- input1$f
    rm(input1)
    hsCRP <- inputw(wave = cbind(hsCRP), f = f)$w
    n1 <- nrow(uric)
    n2 <- nrow(hsCRP)
    if (n1 != n2)
        stop("'uric' and 'hsCRP' time series must have the same length")
    n <- n1
    if (!is.null(flimd)) {
        mag <- round((f)/(flimd[2] - flimd[1]))
        wl <- wl * mag
        if (ovlp == 0)
            ovlp <- 100
        ovlp <- 100 - round(ovlp/mag)
        flim <- flimd
    }
    step <- seq(1, n - wl, wl - (ovlp * wl/100))
    z1 <- matrix(data = numeric((wl) * length(step)), wl, length(step))
    for (i in step) {
        z1[, which(step == i)] <- spec.pgram(cbind(uric[i:(wl +
            i - 1), ], hsCRP[i:(wl + i - 1), ]), spans = c(3,
            3), fast = FALSE, taper = FALSE, plot = FALSE)$coh
    }
    z <- z1[1:(wl/2), ]
    X <- seq(0, n/f, length.out = length(step))
    if (is.null(flim)) {
        Y <- seq(0, f, length.out = nrow(z))
    }
```

FIG. 6A.

CONTINUES IN FIG. 6B

CONTINUES FROM FIG. 6A

```
else {
    fl1 <- flim[1] * nrow(z) * 16/f
    fl2 <- flim[2] * nrow(z) * 16/f
    z <- z[fl1:fl2, ]
    Y <- seq(flim[1], flim[2], length.out = nrow(z))
}

Z <- t(z)
if (plot) {
    Zlim <- range(Z, finite = TRUE)
    if (scale) {
        def.par <- par(no.readonly = TRUE)
        on.exit(par(def.par))
        layout(matrix(c(1, 2), ncol = 2, byrow = TRUE), widths = c(6, 1))
        par(mar = c(5, 4.1, 1, 0), las = 1, cex = 1, bg = colbg,
            col = colaxis, col.axis = colaxis, col.lab = collab)
        filled.contour.modif2(x = X, y = Y, z = Z, levels = collevels,
            nlevels = 20, plot.title = title(main = main,
              xlab = xlab, ylab = ylab), color.palette = palette,
            axisX = axisX, axisY = axisY)
        if (grid)
            grid(nx = NA, ny = NULL, col = colgrid)
        if (colaxis != colgrid)
            abline(h = 0, col = colaxis)
        else abline(h = 0, col = colgrid)
        par(mar = c(5, 1, 4.5, 3), las = 0)
        dBscale(collevels = collevels, palette = palette,
            fontlab = scalefontlab, cexlab = scalecexlab,
            collab = collab, textlab = scalelab, colaxis = colaxis)
    }
    if (scale == FALSE) {
        par(las = 1, col = colaxis, col.axis = colaxis, col.lab = collab,
            , bg = colbg, ...)
        filled.contour.modif2(x = X, y = Y, z = Z, levels = collevels,
            nlevels = 20, plot.title = title(main = main,
              xlab = xlab, ylab = ylab), color.palette = palette,
            axisX = axisX, axisY = axisY, col.lab = collab,
            colaxis = colaxis)
        if (grid)
            grid(nx = NA, ny = NULL, col = colgrid)
        if (colaxis != colgrid)
            abline(h = 0, col = colaxis)
        else abline(h = 0, col = colgrid)
    }
    if (cont) {
        contour(X, Y, Z, add = TRUE, levels = contlevels,
            nlevels = 5, col = colcont, ...)
    }
    invisible(list(time = X, freq = Y, coh = Z))
}
else return(list(time = X, freq = Y, coh = Z))
}
```

*FIG. 6B.*

CONTINUES IN FIG. 6C

CONTINUES FROM FIG. 6B

```
# inits for time series 32 long
t1 <- seq(1:32)

# load bivariate log-return time series for a cardiovascular ischemic event-positive case
ts <- read.csv(file="c:/0_cerdsm/IP/cardiology_uric_hsCRP_crqa/uric_hscrp_ts_p1.csv",
header=TRUE,
         colClasses=c("integer",rep("numeric",4)))
u <- ts$u_ln_rtn
c <- ts$c_ln_rtn plot(t1, c, ty='l', lwd=3, col='red', ylim=c(-1,1))
lines(t1, u, lwd=2, col='blue')

# calculate bivariate coherence by evolutionary locally-stationary wavelet spectral method
X <- matrix(rep(0,64), ncol=2)
X[,1] <- u
X[,2] <- c
X <- as.ts(X)

# raw EWS using Daubechies least-asymmetric wavelet with 4 vanishing moments
# EWS <- mvEWS(X, filter.number=4, kernel.name="daniell", kernel.param=12) ; sometimes fails so prefer # the steps below
EWS <- RawPeriodogram(X, filter.number=4, family="DaubLeAsymm", format=TRUE)

# smoothed EWS using kernel "daniell"
EWS <- Smooth_EWS(EWS, kernel.name="daniell", kernel.param=2)

# correct for the estimator bias
EWS <- CorrectBias(EWS)

# adjust estimate for positive definite matrices
EWS <- AdjPositiveDef(EWS)

# calculate variance and percentiles
SpecVar <- varEWS(EWS)
Q025 <- Asymp_Quantile(object=EWS, var=SpecVar, prob=0.025)
Q975 <- Asymp_Quantile(object=EWS, var=SpecVar, prob=0.975)

# plot evolutionary wavelet spectrum estimated time series
plot(EWS, style=3, info=c(1,2), ylab="Rescaled Time Series", diag=FALSE, Int.lower=Q025,
Int.upper=Q975)

# partial coherence
PRHO <- coherence(EWS, partial=TRUE)
plot(PRHO, style=3, info=c(1,2), ylab="Partial Coherence", diag=FALSE, col='red', lwd=3)

# calculate continuous coherence with 2D time-freq plot
contin_coh <- ccoh_u_c(u, c, f=32, wl=8)

# add small amount of Gaussian noise to prevent matrix singularities in subsequent steps
set.seed(1239)
cn <- c + rnorm(32, 0.0, 0.001)
un <- u + rnorm(32, 0.0, 0.001)
```

*FIG. 6C*

CONTINUES IN FIG. 6D

CONTINUES FROM FIG. 6C

```
# compute transfer entropy hsCRP dep on uric
te_c_u <- computeTE(cn, un, embedding=3, k=1, method="MI_diff", safetyCheck=TRUE)
    # 0.53 strong evidence transfer of entropy uric to hsCRP
te_c_u compute transfer entropy uric dep on hsCRP
te_u_c <- computeTE(un, cn, embedding=3, k=1, method="MI_diff", safetyCheck=TRUE)
    # -0.27 substantial evidence of TE from uric to hsCRP
te_u_c

# load bivariate time series for a cardiovascular ischemic event-negative case
ts <- read.csv(file="c:/0_cerdsm/IP/cardiology_uric_hsCRP_crqa/uric_hscrp_ts_n1.csv",
header=TRUE,
        colClasses=c("integer",rep("numeric",4)))
u <- ts$u_ln_rtn
c <- ts$c_ln_rtn plot(t1, c, ty='l', lwd=3, col='red', ylim=c(-1,1))
lines(t1, u, lwd=2, col='blue')

# calculate bivariate coherence by evolutionary locally-stationary wavelet spectral method
X <- matrix(rep(0,64), ncol=2)
X[,1] <- u
X[,2] <- c
X <- as.ts(X)

# raw EWS using Daubechies least-asymmetric wavelet with 4 vanishing moments
# EWS <- mvEWS(X, filter.number=4, kernel.name="daniell", kernel.param=12) ; sometimes fails so prefer the steps below
EWS <- RawPeriodogram(X, filter.number=4, family="DaubLeAsymm", format=TRUE)

# smoothed EWS using kernel "daniell"
EWS <- Smooth_EWS(EWS, kernel.name="daniell", kernel.param=2)

# correct for the estimator bias
EWS <- CorrectBias(EWS)

# adjust estimate for positive definite matrices
EWS <- AdjPositiveDef(EWS)

# calculate variance and percentiles
SpecVar <- varEWS(EWS)
Q025 <- Asymp_Quantile(object=EWS, var=SpecVar, prob=0.025)
Q975 <- Asymp_Quantile(object=EWS, var=SpecVar, prob=0.975)

# plot evolutionary wavelet spectrum estimated time series
plot(EWS, style=3, info=c(1,2), ylab="Rescaled Time Series", diag=FALSE, Int.lower=Q025, Int.upper=Q975)
```

FIG. 6D.

CONTINUES IN FIG. 6E

CONTINUES FROM FIG. 6D

```
# partial coherence
PRHO <- coherence(EWS, partial=TRUE)
plot(PRHO, style=3, info=c(1,2), ylab="Partial Coherence", diag=FALSE, col='red', lwd=3)

# calculate continuous coherence with 2D time-freq plot
contin_coh <- ccoh_u_c(u, c, f=32, wl=8)

# add small amount of Gaussian noise to prevent matrix singularities in subsequent steps
set.seed(1239)
cn <- c + rnorm(32, 0.0, 0.001)
un <- u + rnorm(32, 0.0, 0.001)

# compute transfer entropy hsCRP dep on uric
te_c_u <- computeTE(cn, un, embedding=3, k=1, method="MI_diff", safetyCheck=TRUE)
    # 0.03 no evidence transfer of entropy uric to hsCRP
te_c_u compute transfer entropy uric dep on hsCRP
te_u_c <- computeTE(un, cn, embedding=3, k=1, method="MI_diff", safetyCheck=TRUE)
    # 0.41 substantial evidence of entropy transfer hsCRP to uric, and no evidence of TE from uric to
hsCRP
te_u_c

# define example u time series with power mostly in low-freq bands initially, then some jumps and
# increased bandwidth later
# set.seed(1239)
# u <- round(rnorm(32, 0, 0.4),2)
u <- c(0.04,  0.08, -0.02, -0.07,  0.01,  0.08, 0.12,  0.20,  0.07, -0.02, -0.03, 0.04, 0.25, 0.40, 0.01, -0.08,
       -0.91, -0.89, -0.74, -0.56, -0.39, -0.22, 0.02, -0.04, -0.16, 0.02, -0.20, 0.71, 0.50, 0.52, 0.79, -0.48)
mean(u)
sd(u)
hist(u)
lm(u ~ t1)
# Coefficients:
# (Intercept)    t1
-0.0705    0.0025 create exponentially-weighted moving-average c time series where c lags u by about 20 hours
c <- rep(0, 32)
for (i in 4:32) {
  c[i] <- round(0.4*u[i] + 0.3*u[i-1] + 0.2*u[i-2] + 0.1*u[i-3], 2)
}
c[1] <- -0.02
c[2] <- 0.05
c
# [1] -0.02  0.05  0.00 -0.01 -0.01  0.02  0.07  0.13  0.12  0.06  0.02 0.01 0.10 0.24 0.18  0.08
# [17] -0.35 -0.64 -0.75 -0.72 -0.56 -0.39 -0.19 -0.09 -0.09 -0.05 -0.11 0.21 0.38 0.48 0.64  0.20
```

*FIG. 6E.*

CONTINUES IN FIG. 6F

CONTINUES FROM FIG. 6E

```
mean(c)
sd(c)
hist(c)
lm(c ~ t1)
# Coefficients:
# (Intercept)    t1
-0.0713    0.0024 both u and c are approximately gaussian, demeaned, and detrended, but c lags u
plot(t1, c, ty='l', lwd=3, col='red', ylim=c(-1,1))
lines(t1, u, lwd=2, col='blue')

# calculate bivariate coherence by evolutionary locally-stationary wavelet spectral method
X <- matrix(rep(0,64), ncol=2)
X[,1] <- u
X[,2] <- c
X <- as.ts(X)

# raw EWS using Daubechies least-asymmetric wavelet with 4 vanishing moments
# EWS <- mvEWS(X, filter.number=4, kernel.name="daniell", kernel.param=12) ; sometimes fails so prefer # the steps below
EWS <- RawPeriodogram(X, filter.number=4, family="DaubLeAsymm", format=TRUE)

# smoothed EWS using kernel "daniell"
EWS <- Smooth_EWS(EWS, kernel.name="daniell", kernel.param=2)

# correct for the estimator bias
EWS <- CorrectBias(EWS)

# adjust estimate for positive definite matrices
EWS <- AdjPositiveDef(EWS)

# calculate variance and percentiles
SpecVar <- varEWS(EWS)
Q025 <- Asymp_Quantile(object=EWS, var=SpecVar, prob=0.025)
Q975 <- Asymp_Quantile(object=EWS, var=SpecVar, prob=0.975)

# plot evolutionary wavelet spectrum estimated time series
plot(EWS, style=3, info=c(1,2), ylab="Rescaled Time Series", diag=FALSE, Int.lower=Q025, Int.upper=Q975)

# partial coherence
PRHO <- coherence(EWS, partial=TRUE)
plot(PRHO, style=3, info=c(1,2), ylab="Partial Coherence", diag=FALSE, col='red', lwd=3)

# calculate continuous coherence with 2D time-freq plot
contin_coh <- ccoh_u_c(u, c, f=32, wl=8)

# add small amount of Gaussian noise to prevent matrix singularities in subsequent steps
set.seed(1239)
cn <- c + rnorm(32, 0.0, 0.001)
un <- u + rnorm(32, 0.0, 0.001)
```

FIG. 6F.

CONTINUES IN FIG. 6G

CONTINUES FROM FIG. 6F

```
# compute transfer entropy hsCRP dep on uric
te_c_u <- computeTE(cn, un, embedding=3, k=1, method="MI_diff", safetyCheck=TRUE) # 0.34 some
evidence transfer of entropy uric to hsCRP
te_c_u compute transfer entropy uric dep on hsCRP
te_u_c <- computeTE(un, cn, embedding=3, k=1, method="MI_diff", safetyCheck=TRUE) # -0.03 no
evidence of entropy transfer hsCRP to uric, but some evidence of TE from uric to hsCRP
te_u_c

# create another example u time series that is small-amplitude and low-freq only
# set.seed(1239)
# u <- round(rnorm(32, 0, 0.05),2)
u <- c(0.02,  0.03, 0.01, 0.01, -0.03, -0.05, -0.08, -0.06, -0.03, 0.00,  0.03, -0.07,  0.01, -0.09, -0.02,  0.03,
       0.05, -0.11, 0.00, 0.00, -0.02, -0.05,  0.00, -0.03, -0.02, 0.09, -0.01,  0.06, -0.11,  0.00, -0.06, -0.06)
mean(u)
sd(u)
hist(u)
lm(u ~ t1)
# Coefficients:
# (Intercept)      t1
-0.0321      0.0009 create c time series where c explicitly lags u by 24 hours but with slightly different amplitude and
some Gaussian noise
c <- rep(0, 32)
set.seed(1239)
for (i in 2:32) {
  c[i] <- round(1.1*u[i-1] + rnorm(1, 0, 0.02), 2)
}
c[1] <- 0.02
c
# [1]  0.02 -0.14  0.04  0.02 -0.08 -0.12  0.00 -0.09  0.02  0.04 -0.10  0.01 -0.05 -0.13 -0.03  0.05
[17] 0.08 -0.17  0.00  0.00 -0.03 -0.07  0.00 -0.04 -0.03  0.13 -0.01  0.09 -0.17  0.00 -0.09  0.15 mean(c)
sd(c)
hist(c)
lm(c ~ t1)
# Coefficients:
# (Intercept)      t1
-0.0476      0.0016 both u and c are approximately gaussian, demeaned, and detrended, but c lags u
plot(t1, c, ty='l', lwd=3, col='red', ylim=c(-1,1))
lines(t1, u, lwd=2, col='blue')
# calculate bivariate coherence by evolutionary locally-stationary wavelet spectral method
X <- matrix(rep(0,64), ncol=2)
X[,1] <- u
X[,2] <- c
X <- as.ts(X)
```

*FIG. 6G.*

CONTINUES IN FIG. 6H

CONTINUES FROM FIG. 6G

```
# raw EWS using Daubechies least-asymmetric wavelet with 4 vanishing moments
# EWS <- mvEWS(X, filter.number=4, kernel.name="daniell", kernel.param=12) ; sometimes fails so
prefer the steps below
EWS <- RawPeriodogram(X, filter.number=4, family="DaubLeAsymm", format=TRUE)
# smoothed EWS using kernel "daniell"
EWS <- Smooth_EWS(EWS, kernel.name="daniell", kernel.param=2)
# correct for the estimator bias
EWS <- CorrectBias(EWS)

# adjust estimate for positive definite matrices
EWS <- AdjPositiveDef(EWS)
# calculate variance and percentiles
SpecVar <- varEWS(EWS)
Q025 <- Asymp_Quantile(object=EWS, var=SpecVar, prob=0.025)
Q975 <- Asymp_Quantile(object=EWS, var=SpecVar, prob=0.975)

# plot evolutionary wavelet spectrum estimated time series
plot(EWS, style=3, info=c(1,2), ylab="Rescaled Time Series", diag=FALSE, int.lower=Q025,
int.upper=Q975)

# partial coherence
PRHO <- coherence(EWS, partial=TRUE)
plot(PRHO, style=3, info=c(1,2), ylab="Partial Coherence", diag=FALSE, col='red', lwd=3)

# calculate continuous coherence with 2D time-freq plot
contin_coh <- ccoh_u_c(u, c, f=32, wl=8)

# add small amount of Gaussian noise to prevent matrix singularities in subsequent steps
set.seed(1239)
cn <- c + rnorm(32, 0.0, 0.001)
un <- u + rnorm(32, 0.0, 0.001)
# compute transfer entropy hsCRP dep on uric
te_c_u <- computeTE(cn, un, embedding=3, k=1, method="MI_diff", safetyCheck=TRUE) # 0.38 some
evidence of transfer of entropy uric to hsCRP
te_c_u compute transfer entropy uric dep on hsCRP
te_u_c <- computeTE(un, cn, embedding=3, k=1, method="MI_diff", safetyCheck=TRUE) # 0.06
transfer of entropy hsCRP to uric is weak or indeterminate
te_u_c re-use u create c time series where c is entirely Gaussian noise unrelated to u
set.seed(1031)
c <- round(1.1*rnorm(32, 0, 0.05),2)
c
# [1]  0.05  0.01 -0.01 -0.03  0.02  0.08  0.01 -0.10 -0.05  0.04  0.07  0.08  0.03 -0.01  0.01  0.01
# [17] -0.05  0.10 -0.01  0.02  0.06  0.05 -0.05  0.03 -0.03 -0.10 -0.05 -0.03 -0.04 -0.06  0.01 -0.09
```

FIG. 6H.

CONTINUES IN FIG. 6I

CONTINUES FROM FIG. 6H

```
mean(c)
sd(c)
hist(c)
lm(c ~ t1)
# Coefficients:
# (Intercept)      t1
0.0322     -0.0020 cor(u,c)
[1] -0.02962427 both u and c are approximately gaussian, demeaned, and detrended, and c independent of u
plot(t1, c, ty='l', lwd=3, col='red', ylim=c(-1,1))
lines(t1, u, lwd=2, col='blue')

# calculate bivariate coherence by evolutionary locally-stationary wavelet spectral method
X <- matrix(rep(0,64), ncol=2)
X[,1] <- u
X[,2] <- c
X <- as.ts(X)

# raw EWS using Daubechies least-asymmetric wavelet with 4 vanishing moments
# EWS <- mvEWS(X, filter.number=4, kernel.name="daniell", kernel.param=12) ; sometimes fails so prefer # the steps below
EWS <- RawPeriodogram(X, filter.number=4, family="DaubLeAsymm", format=TRUE)

# smoothed EWS using kernel "daniell"
EWS <- Smooth_EWS(EWS, kernel.name="daniell", kernel.param=2)

# correct for the estimator bias
EWS <- CorrectBias(EWS)

# adjust estimate for positive definite matrices
EWS <- AdjPositiveDef(EWS)

# calculate variance and percentiles
SpecVar <- varEWS(EWS)
Q025 <- Asymp_Quantile(object=EWS, var=SpecVar, prob=0.025)
Q975 <- Asymp_Quantile(object=EWS, var=SpecVar, prob=0.975)

# plot evolutionary wavelet spectrum estimated time series
plot(EWS, style=3, info=c(1,2), ylab="Rescaled Time Series", diag=FALSE, Int.lower=Q025, Int.upper=Q975)

# partial coherence
PRHO <- coherence(EWS, partial=TRUE)
plot(PRHO, style=3, info=c(1,2), ylab="Partial Coherence", diag=FALSE, col='red', lwd=3)

# calculate continuous coherence with 2D time-freq plot
contin_coh <- ccoh_u_c(u, c, f=32, wi=8)
```

*FIG. 6I.*

CONTINUES IN FIG. 6J

CONTINUES FROM FIG. 6I

.
.
.

```
# add small amount of Gaussian noise to prevent matrix singularities in subsequent steps
set.seed(1239)
cn <- c + rnorm(32, 0.0, 0.001)
un <- u + rnorm(32, 0.0, 0.001)

# compute transfer entropy hsCRP dep on uric
te_c_u <- computeTE(cn, un, embedding=3, k=1, method="MI_diff", safetyCheck=TRUE)
    # 0.27 some evidence of entropy transfer uric to hsCRP
te_c_u compute transfer entropy uric dep on hsCRP
te_u_c <- computeTE(un, cn, embedding=3, k=1, method="MI_diff", safetyCheck=TRUE)
    # 0.13 some evidence of entropy transfer hsCRP to uric
te_u_c te_c_u <- computeTE(cn, un, embedding=2, k=1, method="MI_diff", safetyCheck=TRUE)
    # 0.27 some evidence of entropy transfer uric to hsCRP
te_c_u compute transfer entropy uric dep on hsCRP
te_u_c <- computeTE(un, cn, embedding=2, k=1, method="MI_diff", safetyCheck=TRUE)
    # 0.13 some evidence of entropy transfer hsCRP to uric
te_u_c
```

*FIG. 6J.*

```
###########################################################

# generate receiver operating characteristic (ROC) curves of cardiovascular ischemic event
prediction

##################################################### library(pROC)

ds4 <- read.csv(file="c:/0_cerdsm/IP/cardiology_uric_hsCRP_crqa/roc.csv")
roc1 <- roc(ds4[,1] ~ ds4[,2], percent=TRUE,
# arguments for auc
# partial.auc=c(100, 90), partial.auc.correct=TRUE,
#  partial.auc.focus="sens",
# arguments for ci
  ci=TRUE, boot.n=100, ci.alpha=0.9, stratified=FALSE,
# arguments for plot
#  auc.polygon=TRUE, max.auc.polygon=TRUE,
  plot=TRUE, grid=TRUE, print.auc=TRUE, show.thres=TRUE)
sens.ci <- ci.se(roc1, specificities=seq(0, 100, 5))
plot(sens.ci, type="shape", col="lightblue")
plot(sens.ci, type="bars")

roc(ds4[,1] ~ ds4[,2], ds4, plot=TRUE)

# column-major
dsm <- matrix(c(5,1,2,11), ncol=2)
fisher.test(dsm)
# p-value = 0.01
# odds ratio 27.5
# sensitivity 83% (67 - 99)
# specificity 85% (68 - 100)
# NNT 2
# PPV 71% (51 - 92)
# NPV 92% (79 - 100)
# prev 32%
```

FIG. 7

DETERMINING A CARDIOVASCULAR ISCHEMIC EVENT AND DECISION SUPPORT TOOL

INCORPORATION BY REFERENCE; DISCLAIMER

Each of the following applications are hereby incorporated by reference: U.S. application Ser. No. 16/141,682, filed on Sep. 25, 2018, and U.S. Provisional Application No. 62/562,761, filed on Sep. 25, 2017. The applicant hereby rescinds any disclaimer of claims scope in the parent application(s) or the prosecution history thereof and advises the USPTO that the claims in the application may be broader than any claim in the parent application(s).

BACKGROUND

Major problems in delivery of safe and effective prevention and care services involve deficiencies in the quality and continuity of patient care, including the monitoring of each patient's condition over time. Despite recent advances in electronic health records (EHR) systems, the present state of the art in medical care still does not in general utilize the accruing medical record information for active, prognostic use-cases, to predict the future status or events or outcomes that are likely to materialize for the patient. Instead, in many scenarios the EHR acts mainly as a passive repository for documenting and storing the information that is generated by each provider and each department, which characterizes the current or previous status or outcomes that have already materialized.

During ongoing patient management in situations requiring monitoring for cardiovascular ischemic conditions, each patient may over a period of time see many doctors and many nurses. Such fragmentation of responsibility for the care process challenges the ability of each provider to quickly and accurately grasp the meaning of the constellation of accumulating clinical and laboratory facts about the patient, to understand trends that may be developing in the patient's health status, and to evaluate the urgency of attention that is necessary to effectively address existing or newly developing issues, or to successfully prevent potential adverse events and complications. In the case of patients with AMI or stroke risk, this situation is further complicated by the fact that most cardiovascular risk values of such patients are outside normal limits, such that longitudinal changes or the appropriate actions to take based on them are obscure.

Acute coronary syndrome (ACS) refers to a condition with acute myocardial ischemia and necrosis resulting from severe coronary artery stenosis and even occlusion. It is caused by intracoronary plaque rupture, vasospasm and consequent platelet adhesion, aggregation and secondary thrombosis. This constitutes a serious threat to human life and shows a low aging tendency. The inflammatory response and the stress on the heart itself may participate in the ischemia and instability of atherosclerotic plaque.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

Improved monitoring and decision support technology is provided for human patients who may be prone to coronary artery disease (CAD) or other cardiovascular conditions such as stroke, which may include monitoring or tracking the clinical and physiologic status of a patient at risk of ischemic events. In particular, a mechanism is provided, which may be embodied as a computerized decision support tool, to determine a patient's risk for experiencing a cardiovascular ischemic event at a future time interval based on temporal patterns determined using physiological parameters of the patient such as serum or blood uric acid and/or C-reactive protein (CRP). A forecast or score may be determined indicating whether or not temporal patterns merit intervention to prevent occurrence or reoccurrence of ischemic events, or for determining adherence to or efficacy of treatment or preventive interventions. Based on the forecast or score, appropriate response action such as automatically issuing an alert or notification to a caregiver associated with the patient, may be determined, recommended, or implemented. In some instances, a decision support tool determines or recommends appropriate preventive actions that may be clinically indicated and such that the patient's adherence to effective prevention or treatment regimens promptly yields indicia of reduced risk.

In one embodiment, the mechanism utilizes a time series spectrum analysis to determine a statistical forecast or probability of future ischemic events for a multi-year time horizon. A time series comprised of pairs of measurements of serum or blood high-sensitivity C-reactive protein (hsCRP) and uric acid may be transformed into a frequency-domain spectrum. Based on this, a transfer entropy between hsCRP and uric acid and the bivariate spectral coherence are then determined. Evidence-combining of transfer entropy and coherence values produces an estimate of multi-year risk of ischemic cardiovascular events, despite any concomitant presence of one or more confounding conditions that would normally interfere with the sensitivity and/or specificity of prior art methods of risk estimation in conventional approaches. Based on the generated forecast and/or score, one or more actions may be carried out automatically or may be recommended, such as, without limitation, intervening in the patient's care, modifying a care program for treating the patient, automatically scheduling interventions or consultations with specialist caregivers, or generating notifications such as electronic messages, which may include recommendations, information, alerts, or alarms, based on the forecast which may be emitted or otherwise provided to the caregiver and/or to the patient. Some embodiments may be used for continually tracking a clinical respiratory status of a patient in an ambulatory setting or at home.

In this way, embodiments disclosed herein may enable physicians, nurses and clinical researchers to provide more safe and effective care for each patient, especially those who have a prior history of one or more ischemic events, and in particular those in whom other ischemia risk-determining methods yield excessive false-positive and/or false-negative results. Moreover, recognizing a high risk of an ischemic cardiovascular event far enough in advance of the onset of symptoms can guide rational allocation of resources, including intensified monitoring or treatments that may achieve reduction of risks of ischemic event(s), decreasing frequency of episodes and length-of-stay in acute care institutions, financial savings, or other benefits.

BRIEF DESCRIPTION OF THE DRAWINGS

The present technology is described in detail below with reference to the attached drawing figures, wherein:

FIG. 2 depicts a flow diagram showing a method utilized by a decision support tool for generating a forecast of a cardiovascular ischemic event over a future time interval for a patient, and if needed, implementing one or more response actions based on the generated forecast, in accordance with an embodiment of the present disclosure;

FIGS. 6A-6J illustratively provide an example embodiment of a computer program routine for generating a forecast of a cardiovascular ischemic event over a future time interval for a patient, in accordance with an embodiment of the present disclosure; and FIG. 7 illustratively provides an example embodiment of a computer program routine for generating a receiver operating characteristic (ROC) curve of the forecasting system and method set forth in the technology for an embodiment of the disclosure described in connection with the method of FIG. 2.

DETAILED DESCRIPTION

Figure 1A:
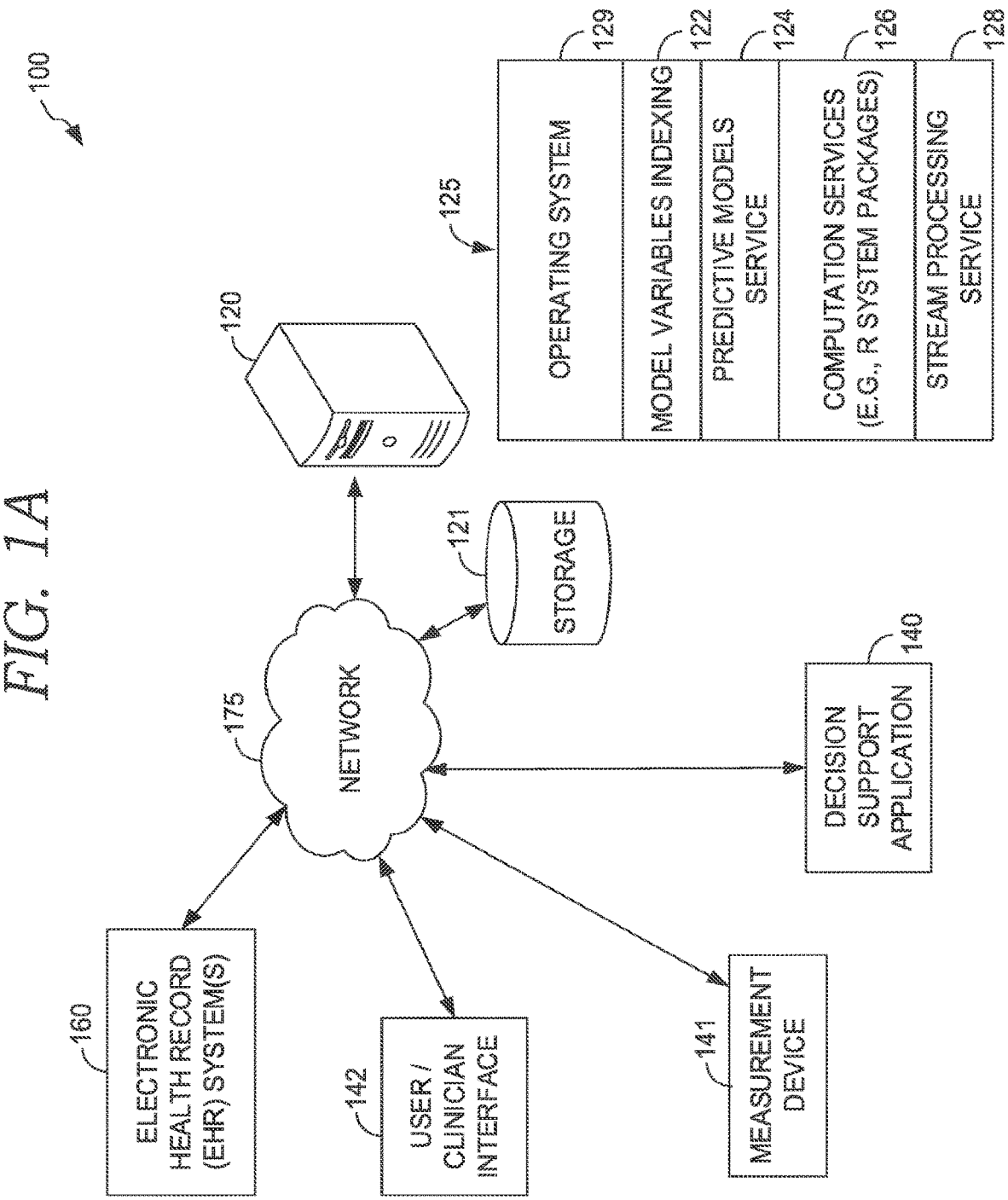
FIGS. 1A and 1B depict aspects of an illustrative architecture suitable for practicing an embodiment of the present disclosure.

The subject matter of the present technology is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the technology may be embodied as, among other things: a method, system, or set of instructions embodied on one or more computer readable media. Accordingly, the embodiments may take the form of a hardware embodiment, a software embodiment, or an embodiment combining software and hardware. In one embodiment, the technology takes the form of a computer-program product that includes computer-usable instructions embodied on one or more computer readable media.

Computer-readable media include both volatile and nonvolatile media, removable and nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other non-transitory memory technology, CD-ROM, digital versatile discs (DVD), holographic media or other optical disc storage, magnetic cassettes, magnetic tape, magnetic disk storage, other magnetic storage devices, and other computer hardware or non-transitory storage devices. These technologies can store data momentarily, temporarily, or permanently.

Aspects of the technology described herein provide improved decision support for the healthcare of patients who are prone to coronary artery disease (CAD) or other cardiovascular conditions such as stroke. In particular, embodiments described herein serially measure the levels of physiological variables such as uric acid (UA) and high-sensitivity C-reactive protein (hsCRP) in patients having hsCRP values in the upper tertile, determine a bivariate time series, and utilize the bivariate time series to generate a novel index of ischemic risk. For instance, embodiments described herein may be utilized for screening or monitoring patients (including patients at home or ambulatory settings or for telemedicine scenarios) and quantitatively determining whether or not quantitatively predicting whether or not temporal patterns in serum or blood uric acid and C-reactive protein (CRP) parameters merit intervention to prevent occurrence or recurrence of ischemic events, or determining adherence to or efficacy of treatment or preventive interventions. In an embodiment, a clinical decision support tool is provided that determines a likelihood, which may be expressed as a score or forecast, of a cardiovascular ischemic event occurring over a future time interval. In some embodiments, the future time interval may be a time duration from the present up to ninety days, six months, or one year. In some embodiments, the future time interval may be a time duration of between approximately one and five years into the future or between one and ten years into the future.

The information utilized for determining the forecast or score may be derived from pairs of measurements of serum or blood high-sensitivity C-reactive protein (hsCRP) and uric acid. This information may be processed and transformed into a frequency-domain spectrum, from which a transfer entropy between hsCRP and uric acid and the bivariate spectral coherence may be determined. Evidence-combining of transfer entropy and coherence values then may be utilized to generate an estimate of multi-year risk of ischemic cardiovascular events, which may be represented as a score or forecast. In particular, the score (or forecast) may include a statistical probability or prediction, which may be used by the decision support tool to determine and/or invoke a particular action in response to the score. For example, based on the generated forecast, one or more actions may be carried out automatically or may be recommended, such as, without limitation, intervening in the patient's care, modifying a care program for treating the patient, automatically scheduling interventions or consultations with specialist caregivers, or generating notifications such as electronic messages, which may include recommendations, information, alerts, or alarms, based on the forecast which may be emitted or otherwise provided to the caregiver and/or to the patient. In some embodiments, a score or indicator or a patient's probability of experiencing a cardiovascular ischemic event in the future may be provided and utilized to determine recommendations regarding intervention or other changes in treatments plans. Intervening actions may also include recommendations or preventive actions that may be clinically indicated, such that the patient's adherence to effective prevention or treatment regimens yields indicia of reduced risk.

More specifically, embodiments disclosed herein provide improved diagnostic and predictive decision support technology to facilitate patient care by generating near-term forecast multi-year risk of ischemic event occurrence or recurrence, which in some embodiments, may be periodically plotted and displayed to show each patient's risk trend during his/her prevention management. Some embodiments may comprise a decision support tool having an interface module for receiving incoming medical data from a patient, a transformation module for transforming the time series of measurement values into forecasted value, and a communication/reporting/display module for presenting one or a series of values pertaining to a patient.

Some embodiments described herein entail a system or method that may optionally utilize automated storage and processing of recorded values on a handheld measuring device or smartphone, plus transmission of data from such devices via wired (such as LAN or telephone, for example) or wireless means (such as Bluetooth, WiFi LAN, or cellular telephony, for example) to remote storage and processing facilities. Patients may then readily and more immediately manage their risk of ischemic events by adapting their dietary intake, exercise regimen, aspirin or other anti-platelet therapy, or other medical interventions. Further, patients may be more likely to adhere to a measurement regimen if they are not required to perform complex, excessively frequent, or long-duration collections, undertake careful dilutions or reagent additions to perform the testing, or transcribe testing results into other records. Accordingly, some embodiments described herein enable such patients, using a simple handheld measurement device and procedure, to avoid pre-analytic errors resulting from blood specimen collection (including failure to obtain specimens at the desired times, or failure to keep the specimen until it can be tested), transport, and storage.

Accordingly, as will be further described, systems and computerized methods are provided to facilitate screening and monitoring patients prone to coronary artery disease (CAD) or other cardiovascular conditions such as stroke, generating a score indicating likelihood of a cardiovascular ischemic event occurring over a future time interval, and providing computer-performed decision support, which may include invoking one or more actions or recommendations. In some embodiments, these systems or methods are incorporated into a decision support tool used for screening, monitoring, and/or treating the patient.

In one aspect, a method embodiment comprises receiving measurements of blood or serum physiological variables, such as serum or blood high-sensitivity C-reactive protein (hsCRP) and uric acid. The measured of blood or serum physiological variable values may be appended to a respective time series representing measurement values of the variables at corresponding date-time stamps. Some embodiments utilize a single time series comprising a plurality of measurements for each entry of the time series. Similarly, a separate time series may be utilized for each measured variable. This for a pair of measured variables, such as uric acid and serum or blood high-sensitivity C-reactive protein, two time series are determined.

A set of time series measurements comprising more recent measurements may be extracted or determined from the time series, and it may be determined whether the time series is of sufficient length. In other words, it may be determined whether a sufficient number of bivariate measurement pairs been acquired. Next, a determination is made regarding whether the extracted or recent time series measurement values have constant values.

Once it has been determined that the recent or extracted time series is of sufficient length and does not have constant values, the time series may be utilized to determine log returns. The time series may further be detrended and demeaned. In particular, a log-return time series may be constructed from each raw time series, and then the method may include demeaning and detrending each log-return time series. From these calculations, a transfer entropy and spectral coherence are determined.

The transfer entropy and spectral coherence then may be combined to generate a composite index representing an ischemic event risk forecast. The forecast may be evaluated against a threshold to determine whether one or more actions should be invoked because the determined likelihood of an ischemic event occurring is sufficiently high. In particular, based on the generated forecast and/or score, one or more actions may be carried out automatically or may be recommended, as described herein. The method may be repeated as needed or if desired after a passage of time, such as every 12 hours, 24 hours, every other day, weekly, monthly, bi-annually, or the like, or may be repeated occasionally or as needed.

As described above, during ongoing patient management in situations requiring monitoring for cardiovascular ischemic conditions, a patient may over a period of time see many doctors and many nurses. In the case of patients with AMI or stroke risk, this situation is further complicated by the fact that most cardiovascular risk values of such patients are outside normal limits, such that longitudinal changes or the appropriate actions to take based on them are obscure.

The consequence of relatively infrequent assessment of indices of endothelial inflammation, such as high-sensitivity C-reactive protein (hsCRP), often in cardiology clinics at intervals of 6 months or more, when combined with the all-too-common fragmentation of the care process with responsibilities divided among dozens of provider personnel most of whom do not have deep or longstanding familiarity with the patient, is that unexpected ischemic events occur or recur to many patients, such that acute care is required. In many such instances, the impending event could have been predicted-provided that more frequent home-testing or laboratory monitoring were acquired in advance; provided that that data were integrated into a suitably accurate personalized predictive model; and provided that the output of the model were effectively communicated to the providers who have the responsibility to intervene and prevent or manage the predicted risk of ischemic events.

Subtle patterns in serum or blood analyte measurements may presage the development of ischemic events. Frequent measurement is a strategy that has often been neglected but is now enabled by the introduction of small, comparatively inexpensive point-of-care testing devices having ergonomics and low complexity compatible with routine testing by the consumer. Many such devices today possess Bluetooth or WiFi or USB communications connectivity so that data can be easily uploaded for analysis and interpretation, and results and recommendations and be quickly presented to both the consumer and to clinicians who are responsible for their care. The use of such devices is enabled by the technology presented in the present disclosure. Further, the use of such small devices, is not well-understood, routine, or conventional in the field of the technology.

The probability distributions of serum or blood analyte signals, such as uric acid and hsCRP, are, in general, non-stationary. When an objective function's minimum is non-stationary, its moving average location drifts and the optimization goal is one of tracking the optimal vector on short sequences of observations or short time-scales or both. In the case of longitudinal monitoring where the status of the patient often changes relatively quickly, the optimum may drift rapidly. Further, the systems that give rise to the measured data tend to embody a chaotic, stochastic process for which least-mean-square or recursive least-square deterministic optimizer that requires estimating a derivative with respect to time does not produce forecasts of adequate accuracy. However, the embodiments described herein are capable of overcoming this problem and thus improve on the conventional technology. In particular, these embodiments can accommodate aperiodic, gappy sampling and rapid-drift non-differentiable processes. Moreover, embodiments of our technology overcome certain drawbacks associated with the conventional technology by providing a means for longitudinally calculating and tracking the patient's risk of ischemic events.

Despite the emphasis by prior art and conventional technology on biomarkers endothelial inflammation, ischemic events may nevertheless form even under conditions of low interleukin-6 (IL-6) or CRP. Conversely, ischemic events may not materialize in subjects whose IL-6 or hsCRP levels are continually elevated, due to any of a wide variety of non-cardiovascular conditions. The conventional approach for testing using serum or blood hsCRP has many problems, including poor specificity or lack of applicability or confounding by other intercurrent or concomitant inflammatory conditions that are not predominantly vascular. These confounding conditions may be either acute or chronic, and they may be either mild or moderate or severe. Some of these confounding conditions include: diabetes mellitus Type 1, aerobic exercise or eccentric and concentric muscle training, gingivitis and periodontal disease, pharyngitis, otitis, sinusitis, rhinitis, pneumonia, asthma, bronchitis, chronic obstructive pulmonary disease (emphysema, bronchiectasis, etc.), autoimmune diseases (psoriasis, lupus, multiple sclerosis, rheumatoid arthritis), celiac disease, inflammatory bowel diseases (Crohn's; ulcerative colitis), diverticulitis, pilonidal cyst, dentures or orthodontic appliances, peptic ulcer disease, vitamin D deficiency, gastroesophageal reflux disease (GERD), achalasia, gastroenteritis, cholelithiasis, hepatitis, cirrhosis, pancreatitis, hemorrhoids, pilonidal cyst, cystitis, urolithiasis, glomerulonephritis, pyelonephritis, chronic prostatitis, epididymitis, pelvic inflammatory disease, endometriosis, polycystic ovary syndrome, uveitis, mastitis and fibrocystic disease, osteoarthritis, bursitis, ankylosing spondylitis, tendonitis, muscular dystrophy, sarcopenia, statin-induced myopathy, gout, sarcoidosis, transplant rejection, Hashimoto's thyroiditis, autoimmune hemolytic anemia, thrombocytopenia purpura, bullous pemphigoid, pemphigus vulgaris, Graves' disease, myasthenia gravis, pernicious anemia, hypertension, congestive heart failure, neoplasms, bacteremia or sepsis, hidradenitis suppurativa, allergic hypersensitivities, eczema, acne vulgaris, hang-nail, felon and paronychia, and inflammation connected with minor puncture or laceration wounds, such as minor scratches or bites from a companion animal. The assortment of potentially confounding conditions is so large and the duration of the confounding, when present, is sufficiently long, such that the rate of false-positive errors arising from the confounding is exceedingly common, so as to significantly impair the accuracy of clinical decision-making for many patients at-risk.

A further problem is that conventional technology for serum or blood hsCRP testing is confounded by concomitant conditions that are not primarily inflammatory conditions. These include: overweight or obesity with increased abdominal adiposity or BMI or waist circumference, tobacco or smoking status, decreased sleep duration, obstructive sleep apnea, and non-alcoholic steatosis of liver.

A still further problem of the conventional technology is that its predictive capability is not associated with a particular time frame such as would facilitate making the results actionable in a manner that would promote the patient's psychological motivation to adhere to prescribed therapy. Accordingly, if no action that the patient takes produces a noticeable change in the residual risk or likelihood of the event's future occurrence, then motivation and adherence are diminished.

Further problems with the conventional technology for determining or predicting ischemic events in a human patient include: (1) degraded precision for measurements of CRP in the upper range of hsCRP levels (within-person coefficient of variation >30% for hsCRP>5 mg/L), which interferes with personalized medical management particularly in patients who manifest the highest levels of risk or who are obese and in whom intensive and reliable decision-making is most needed; (2) degraded precision for measurements of uric acid in the upper range of uric acid levels (within-person coefficient of variation >15% for uric acid >7 mg/dL), which interferes with personalized medical management particularly in patients who manifest the highest levels of risk or who have gout or other conditions (including high-protein diet) in which elevated uric acid concentrations are a prominent feature and in whom intensive and reliable decision-making is most needed; and (3) excessive expense and narrower availability except in metropolitan hospital emergency departments, as is the case with cardiac troponin-T (cTnT) and brain natriuretic peptide (BNP).

Embodiments of the decision support tool disclosed herein solve these and other problems and thus provide improved diagnostic and predictive decision support technology to facilitate patient care. In particular, embodiments restore specificity and applicability of hsCRP-based ischemic risk estimation, even in the case of comorbid chronic inflammatory processes and conditions that are not primarily inflammatory in nature, such as obesity. Additionally, embodiments of the decision support tool afford a valuable statistical sensitivity for classifying ischemic events risk without producing excessive false-positive errors. Specifically, as described herein, serial, paired biochemical measurements of serum or blood uric acid concentration and hsCRP concentration—preferably paired closely in time or synchronously, or, less preferably, sampled in a mixed-frequency regime—may be assembled into time series which, in turn, are subjected to spectral coherence and transfer entropy determinations, for the purpose of assessing whether or not inflammation that is endothelial in origin is present, sufficient to dispose toward future cardiovascular ischemic events.

Furthermore, embodiments of the decision support tool may provide an accurate index of ischemic risk, improving upon the specificity of hsCRP and other biomarkers, without the need for detailed ascertainment of many concomitant factors such as sleep, adiposity, cardiopulmonary fitness, liver function, and so on. Still further, the embodiments utilization of log-return transformation and coherence and transfer entropy methods ameliorates classification errors arising from the imprecisions for both hsCRP and uric acid at the upper range of risk and enables longitudinal theranostic monitoring of therapy to be performed reliably, in persons whose raw hsCRP values are continually elevated or perhaps at or near the upper limit of quantitation (ULOQ), which otherwise impairs decision-making over time. Thus when compared to certain conventional technology and prior approaches that rely on brain natriuretic peptide (BNP) and cardiac troponin T (cTNT) cardiac risk classification which are expensive and not widely available, there is wide availability of hsCRP and uric acid testing in ambulatory walk-in laboratory facilities, and the combined cost of the two tests is $40 or less.

Embodiments described herein further improve upon conventional technology because the present disclosure enables the use of new types of devices and systems. Prior technologies for measuring variables utilized to determine a cardiovascular ischemic event were bulky, technology specific, cost prohibitive, and required particularized training, such as echocardiograms, electrocardiograms, specific types of blood tests, and the like. The present disclosure, however, describes methods that enable the use of smaller, consumer grade electronics (such as handheld devices or smartphones) to collect different types of information that may be processed to predict and diagnose a cardiovascular ischemic event. In this manner, the underlying technology of these smaller devices is improved because they are performing actions that they previously did not perform or they were incapable of performing. Similarly, the use of these small, consumer grade devices for measuring variables utilized to predict or diagnose cardiovascular ischemic events is not generally performed in the art, as conventional methods used some of the prior technologies described above. For this reason, the use these devices is not well-understood, routine, or conventional.

Additionally, the present disclosure provides for an improvement to the underlying technology of electronic medical record systems. As noted above, electronic medical record systems do not generally use accrued medical record information for active, prognostic use-cases, to predict the future status or events or outcomes likely to materialize for a patient. Instead, in many scenarios, the electronic medical record system acts mainly as a passive repository for documenting and storing the information that is generated by each provider and each department, which characterizes the current or previous status or outcomes that have already materialized. Embodiments provided herein may utilize the electronic medical record system, not just as a repository for information, but as an active, analytical tool for diagnosing or predicting a cardiovascular ischemic event. Not only does this improve the medical record system itself, but it is also method of using the systems in a manner that is not well-understood, routine, or conventional.

Even further still, in contrast to approaches in the conventional technology, the embodiments described herein do not require measuring arterial anatomy by invasive or imaging modalities. Rather, we have discovered that surrogate variables that have a strong statistical association with the process are sufficient to be used as inputs for the processes implemented in the embodiments of our decision support tool.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the technology. Thus for readability, we show and reference items in the singular (while fully contemplating, where applicable, the plural).

As shown in FIG. 1, a block diagram is provided showing aspects of an example computing system architecture suitable for implementing an embodiment of this disclosure and designated generally as example operating environment 100. Example operating environment 100 provides an aspect of a computerized system for compiling and/or running aspects of this disclosure including monitoring, determining, and/or predicting a future occurrence of an ischemic event and decision support technology to facilitate caring for patients who may be prone to experience an ischemic event.

Operating environment 100 is one example of a suitable environment and system architecture for implementing an embodiment of the disclosure. Other arrangements and elements can be used in addition to or instead of those shown, and some elements may be omitted altogether for the sake of clarity. Further, as with operating environment 100, many of the elements described herein are functional entities that may be implemented as discrete or distributed components or in conjunction with other components, and in any suitable combination and location. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for system components or steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer (i.e., computing device) as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Moreover, the components of operating environment 100, functions performed by these components, or services carried out by these components may be implemented at appropriate abstraction layer(s) such as the operating system layer, application layer, hardware layer, etc., of the computing system(s). Alternatively, or in addition, the functionality of these components and/or the embodiments described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. Additionally, although functionality is described herein with regards to specific components shown in example system 200, it is contemplated that in some embodiments functionality of these components can be shared or distributed across other components.

Environment 100 includes one or more electronic health record (EHR) systems, such as EHR system(s) 160 communicatively coupled to network 175, which is communicatively coupled to computer system 120. In some embodiments, components of environment 100 that are shown as distinct components may be embodied as part of or within other components of environment 100. For example, EHR system(s) 160 may comprise one or a plurality of EHR systems such as hospital EHR systems, health information exchange EHR systems, clinical genetics/genomics systems, ambulatory clinic EHR systems, psychiatry/neurology EHR systems, insurance, collections or claims records systems; and may be implemented in or as a part of computer system 120. Similarly, EHR system(s) 160 may perform functions for two or more of types of EHR systems (not shown). EHR system(s) 160 also may include records of urinalysis variables obtained via one or more measurement apparati, tests, or screenings, such as measurement device 141. may perform functions for two or more of types of EHR systems (not shown). In an embodiment, EHR system(s) 160 includes historical claims data for health services, apportionment data, and related health services financial data.

In some embodiments of the technologies described herein, aspects of a decision support tool for patients having or at risk for a cardiovascular ischemic occurrence or recurrence may utilize data about a population of patients derived from patient EHR or other records information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system (s) 160 include one or more data stores of health-related records, which may be stored on storage 121, and may further include one or more computers or servers that facilitate the storing and retrieval of the health records. In some embodiments, EHR system(s) 160 and/or other records systems may be implemented as a cloud-based platform or may be distributed across multiple physical locations. EHR system(s) 160 may further include record systems, which store real-time or near real-time patient (or user) information, such as wearable sensor or monitor, bedside, laboratory, or in-home patient monitors or sensors, for example, such as measurement device 141.

Example operating environment 100 further includes a user/clinician interface 142 and decision support application 140, each communicatively coupled through network 175 to an EHR system 160. Although environment 100 depicts an indirect communicative coupling between interface 142 and application 140 with EHR system 160 through network 175, it is contemplated that an embodiment of interface 142 or application 140 are communicatively coupled to EHR system 160 directly. An embodiment of decision support application 140 comprises a software application or set of applications (which may include programs, routines, functions, or computer-performed services) residing on a client computing device (or distributed in the cloud and on a client computing device) such as a personal computer, laptop, smartphone, tablet, or mobile computing device. In an embodiment, the application is a Web-based application or applet, and may be used to provide or manage user services provided by an embodiment of the technologies described herein, which may be used by a caregiver or screener to provide, for example, information about the likelihood of a specific patient or population of patients to be undergoing deterioration of respiratory functioning or to experience respiratory deterioration at a future time, and may further include a degree or level of deterioration or likely deterioration. In some embodiments, application 140 includes or is incorporated into a computerized decision support tool, as described herein. Further, some embodiments of application 140 utilize user/clinician interface 142.

In some embodiments, application 140 and/or interface 142 facilitates accessing and receiving information from a user or health care provider about a specific patient or set of patients, according to the embodiments presented herein. Embodiments of application 140 also may facilitate accessing and receiving information from a user or health care provider about a specific patient, caregiver, or population including historical data; health care resource data; variables measurements, time series, and predictions (including plotting or displaying the determined outcome and/or issuing an alert) described herein; or other health-related information, and facilitates the display of results, recommendations, or orders, for example. For instance, in an embodiment this information may comprise pairs of measurements of serum or blood high-sensitivity C-reactive protein (hsCRP) and uric acid or generated estimate(s) of multi-year risk of ischemic cardiovascular events for a patient or group of patients, and may further include corresponding notifications, recommendations, care plan changes, or orders. In an embodiment, application 140 also facilitates receiving orders, staffing scheduling, or queries from a user, based on the results of monitoring and/or forecasted outputs, which may in some embodiments utilize user interface 142. Decision-Support application 140 may also be used for providing diagnostic services or evaluation of the performance of various embodiments.

In some embodiments, user/clinician interface 142 may be used with application 140, such as described above. One embodiment of user/clinician interface 142 comprises a user interface that may be used to facilitate access by a user (including a clinician/caregiver such as a medical caregiver, physical therapist, or the like) to a score or prediction determined according to the technologies described herein, including information indicating a likelihood that a patient is experiencing or will experience a cardiovascular ischemic event, or other aspects of forecasts for ischemic events described herein. One embodiment of interface 142 takes the form of a graphical user interface and application, which may be embodied as a software application (e.g., decision support application 140) operating on one or more mobile computing devices, tablets, smartphones, front-end terminals in communication with back-end computing systems, laptops, or other computing devices. In an embodiment, the application includes the PowerChart® software manufactured by Cerner Corporation. In an embodiment, interface 142 includes a Web-based application (which may take the form of an applet or app) or set of applications usable to manage user services provided by an embodiment of the technologies described herein.

In some embodiments, interface 142 may facilitate providing the output of the determined forecast(s), probabilities (or score), recommendations, scheduling orders, providing instructions (such as measuring, recording, and/or otherwise obtaining blood, serum, uric acid, or other physiological variable measurements), confirmations or notifications (such as confirmation that information has been received or notifications that information has not been received and there may be an error in the measuring instrument user operation of a measurement device or measurement procedure), reminders (such as notifications to obtain a physiological measurement sample), or outputs of other actions described herein, as well as logging and/or receiving other feedback from the user/caregiver, in some embodiments. In an embodiment, interface 142 also facilitates receiving orders for the patient from the clinician/user, based on the results of monitoring and predictions. Interface 142 also may be used for providing diagnostic services or evaluation of the performance of various embodiments.

Example operating environment 100 includes measurement device 141 communicatively coupled through network 175 to an EHR system 160. The term measurement is used broadly herein, and it is contemplated that in some embodiments, measurement device 141 may not perform measurement but may receive information about physiological parameters (such as blood, serum, or uric acid variables) which may be measured, observed, or otherwise recorded. Embodiments of measurement device 141 may comprise one or more sensors, such as sensor(s), an interface component, and/or processing/communications component (not shown). In some embodiments, measurement device 141 may comprise a Nesco NW-01 MultiCheck® hand-held instrument for measuring blood uric acid and/or a VITROS 5-FS® Chemistry System for measuring hsCRP. In some embodiments, these measurement device(s) 141 may comprise Bluetooth or wireless communication data-transfer capability and may be wirelessly communicatively coupled with an application on a computing device, such as a smartphone running an app. For example, in one embodiment actually reduced to practice and described below, measurement device 141 comprises a Nesco NW-01 Multi-Check® hand-held instrument and may be configured to transmit the blood uric acid measurements via Bluetooth radio to a nearby cellphone (which may operate as computer system 120 or carry out some or all of the process performed by computer system 120 described herein) for communication to EHR(s) 160.

Embodiments of measurement device 141 may store user-derived data locally or communicate data over network 175 to be stored remotely. Some embodiments of measurement device 141 include a monitor interface, which may be embodied as I/O such as buttons and sounds emitted from the measurement device 141, its firmware or software application or app operating on a user's mobile device or computer system 120, and in an embodiment may facilitate uploading of measured (or recorded, or otherwise received) information from measurement device 141 to computer system 120.

Additionally, some embodiments of measurement device 141 include functionality for processing user-derived information locally or for communicating the information to computer system 120, where it is processed. In some embodiments, the processing may be carried out or facilitated by one or more software agents, as described below. In some embodiments the processing functionality, performed on measurement device 141 and/or computer system 120 includes pre-processing and/or signal conditioning, such as removing noise or erroneous information.

Example operating environment 100 further includes computer system 120, which may take the form of one or more servers, and which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, aspects of application 140 or interface 142 may operate on or utilize computer system 120. Similarly, a portion of computing system 120 may be embodied on user interface 142, application 140, and/or EHR system(s) 160. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local services or may be distributed across one or more components of operating environment 100, in the cloud, on one or more personal computers or servers such as system 120, and/or a computing device running interface 142 or application 140. In some embodiments, interface 142 and/or application 140 operate in conjunction with software stack 125.

In embodiments, model variables indexing (or mapping) service 122 facilitate retrieving patient physiological variables, which may include frequent item sets, extracting database records, and/or cleaning the values of variables in records. For example, service 122 may perform functions for synonymic discovery, indexing or mapping variables in records, or mapping disparate health systems' ontologies, such as determining that a particular medication frequency of a first record system is the same as another record system. Predictive models service 124 comprises computing services or routines for forecasting likelihood of an ischemic event, which may be developed and implemented according to the method described in connection to FIG. 2. In some embodiments, services 122 and 124 may invoke computation services 126.

Computation services 126 may perform statistical or computing operations, and may include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services, and R-system modules or packages such as packages mvLSW, for performing processing of multivariate time series with wavelets including estimation of the multivariate evolutionary wavelet spectrum (mvEWS), local coherence and local partial coherence; seewave for performing processing time waves including spectral content, frequency coherence, and spectrograms; and TransferEntropy for performing estimation of the transfer entropy from one time series to another.

Computation services 126 also may include natural language processing services (not shown) such as Discern nCode™ developed by Cerner Corporation, or similar services. In an embodiment, computation services 126 include the services or routines, which may be embodied as one or more software agents or computer software routines such as the example embodiments of computer program routines illustratively provided in FIGS. 6A-I and FIG. 7. Computation services 126 also may include services or routines for utilizing one or more prediction models such as described in connection to FIG. 2 and the example computer program routines illustratively provided in FIGS. 6A-6I and FIG. 7. In some embodiments, computation services 126 use EHR system(s) 160, model data and model storage services (not shown), and/or other components of example operating environment 100, and may also include services to facilitate receiving and/or pre-processing physiological data. For instance, model data and model storage services may be utilized to perform services for facilitating storage, retrieval, and implementation of the forecasting models described herein and of the data used in the models.

Some embodiments of stack 125 may further comprise services for utilizing an Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 125 may further comprise one or more services stream processing service(s) 128. For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the technology also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
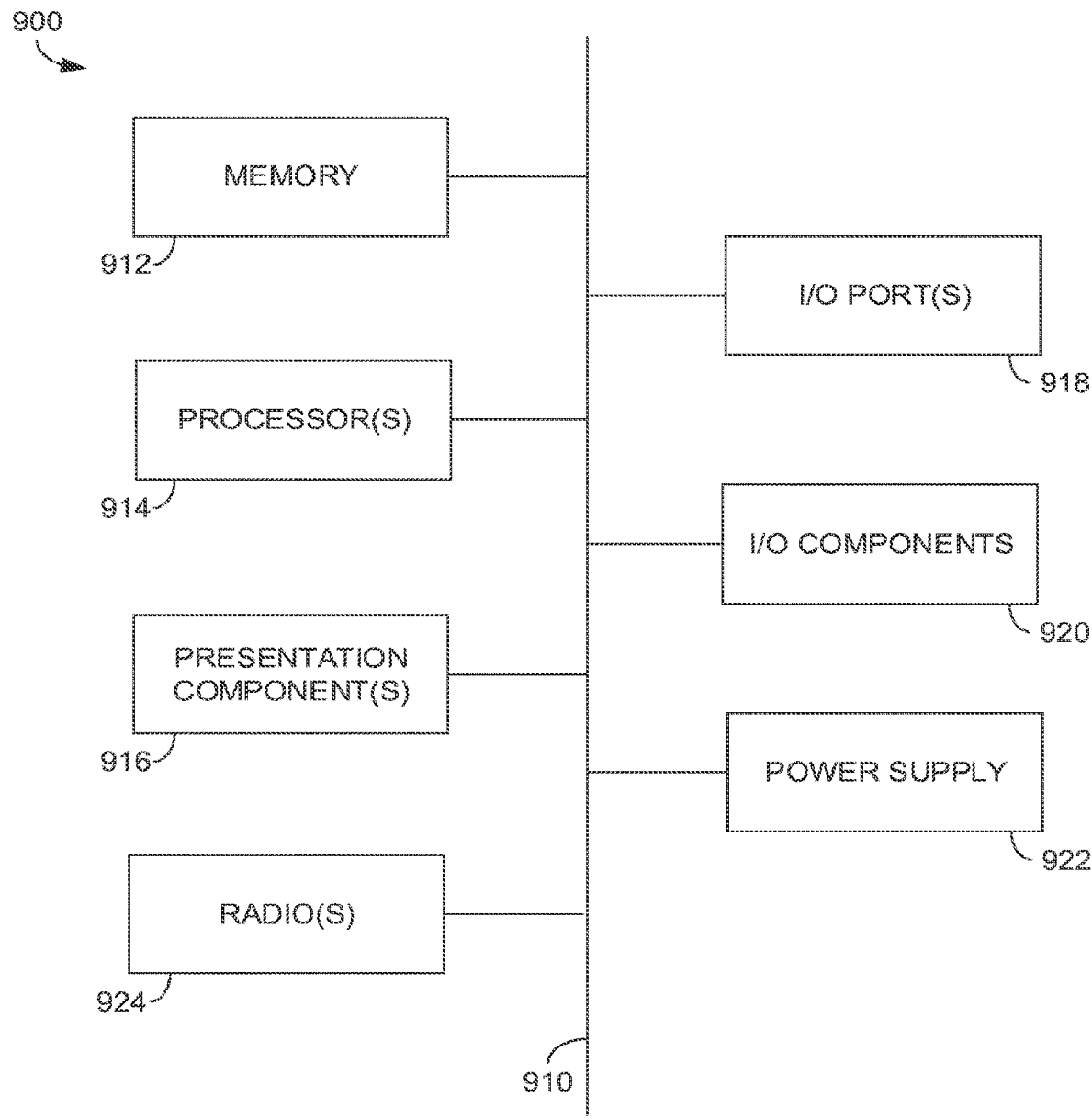

Turning briefly to FIG. 1B, there is shown one example embodiment of computing system 900 representative of a system architecture that is suitable for computer systems such as computer system 120. Computing device 900 includes a bus 910 that directly or indirectly couples the following devices: memory 912, one or more processors 914, one or more presentation components 916, input/output (I/O) ports 918, input/output components 920, radio 924, and an illustrative power supply 922. Bus 910 represents what may be one or more busses (such as an address bus, data bus, or combination thereof). Although the various blocks of FIG. 1B are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1B is merely illustrative of an example computing system architectures that can be used in connection with one or more embodiments of the present disclosure. Distinction is not made between such categories as "workstation," "server," "laptop," "hand-held device," etc., as all are contemplated within the scope of FIG. 1B and reference to "computing system."

Computing system 900 typically includes a variety of computer-readable media. Computer-readable media can be any available media that can be accessed by computing system 900 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 900. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above may be included within the scope of computer-readable media.

Memory 912 includes computer-storage media in the form of volatile and/or nonvolatile memory. The memory may be removable, non-removable, or a combination thereof. Exemplary hardware devices include solid-state memory, hard drives, optical-disc drives, etc. Computing system 900 includes one or more processors that read data from various entities such as memory 912 or I/O components 920. Presentation component(s) 916 present data indications to a user or other device. Exemplary presentation components include a display device, speaker, printing component, vibrating component, etc.

In some embodiments, computing system 924 comprises radio(s) 924 that facilitates communication with a wireless-telecommunications network. Illustrative wireless telecommunications technologies include CDMA, GPRS, TDMA, GSM, LTE, WiMAX, and the like. Radio 924 may additionally or alternatively facilitate other types of wireless communications including Wi-Fi, Bluetooth, NFC, other types of RF communication, light, infrared, or the like. As can be appreciated, in various embodiments, radio 924 can be configured to support multiple technologies and/or multiple radios can be utilized to support multiple technologies.

I/O ports 918 allow computing system 900 to be logically coupled to other devices, including I/O components 920, some of which may be built in. Illustrative components include a microphone, joystick, game pad, satellite dish, scanner, printer, wireless device, etc. The I/O components 920 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 900. The computing system 900 may be equipped with depth cameras, such as stereoscopic camera systems, infrared camera systems, RGB camera systems, touchscreen technology, and combinations of these, for gesture detection and recognition. Additionally, the computing system 900 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Turning now to FIG. 2, a flow diagram is provided that illustrates a method 200 for generating a forecast of a cardiovascular ischemic event, such as an occurrence or recurrence, over a future time interval for a patient. In some embodiments successive forecasts may be generated for a target patient and the successive forecasts then may be combined into a composite forecast. At a high level, and a described above, embodiments of the technologies described herein may facilitate screening and monitoring patients prone to coronary artery disease (CAD) or other cardiovascular conditions such as stroke, generating a score indicating likelihood of a cardiovascular ischemic event occurring over a future time interval, and providing computer-performed decision support, which may include invoking one or more actions or recommendations. In some embodiments, these systems or methods are incorporated into a decision support tool used for screening, monitoring, and/or treating the patient.

With reference to FIG. 2, C-reactive protein (CRP) is an acute phase reactant protein involved in the body's immune response. It is produced by the stimulation of liver and epithelial cells by inflammatory factors and cytokines, including interleukin-6 (IL-6). Hs-CRP may be used as a sensitive biomarker that can reflect the intensity of ongoing inflammation and the stability of atherosclerotic plaque. Recent epidemiological and experimental data on C-reactive protein, the most extensively studied marker of systemic inflammation, produced in the liver in response to interleukin-6, has cast some doubt on its clinical utility and causal involvement in atherogenesis. However, a large number of studies still strongly support C-reactive protein as an independent predictor of future cardiovascular risk and a potent proatherogenic agent. Among all markers of inflammation studied to date, C-reactive protein seems the most suitable one for use in clinical practice.

Despite changes in lifestyle and the use of effective pharmacologic interventions to lower cholesterol levels, coronary heart disease remains the major cause of morbidity and mortality in the developed world. Cholesterol screening fails to identify almost 50% of those individuals who will present with acute coronary syndromes. Recent evidence from laboratory and prospective clinical studies demonstrates that atherosclerosis is not simply a disease of lipid deposition, but rather is an inflammatory process with highly specific cellular and molecular responses. The clinical utility of inflammatory markers has been examined in a variety of atherothrombotic diseases. Because C-reactive protein is highly stable in stored samples, and automated and robust analytical systems for its measurement are available, it has become a widely examined inflammatory marker. Recently, small bench-top instruments capable of accurately measuring hsCRP in a few minutes in microliter specimens have become available. Small bench-top and hand-held instruments for measuring uric acid in microliter specimens have also become available.

Uric acid is the final oxidation product of purine catabolism in humans and primates. It has long been conjectured that the antioxidant properties of uric acid might be protective against aging, oxidative stress, and oxidative cell injury. However, recent epidemiological and clinical evidences suggest that hyperuricemia might be a risk factor for cardiovascular disease, where increased oxidative stress plays an important pathophysiological role. Many large epidemiological studies have confirmed a positive association between serum uric acid levels and risk of coronary heart disease (CHD) or cardiovascular disease (CVD) in the general population and in those with stroke, diabetes, or heart failure.

Uric acid is statistically correlated with many of the established risk factors for cardiovascular disease, including hypertension, hyperlipidemia, obesity, and pre-existing disease. Epidemiological evidence suggests that elevated uric acid not only is a correlate of these but is also an independent predictor of CVD in subjects with hypertension and established vascular disease. There is as yet little evidence so far to indicate that lowering uric acid levels with drug treatment has a beneficial effect on CVD outcome.

However, analyses of uric acid levels may nonetheless provide useful prognostic information in subjects with hypertension, cardiovascular disease, or metabolic syndrome. All these conditions are thought to be mediated by oxidative stress. In that regard, differentiation of mature adipocytes is associated with increased production of reactive oxygen species (ROS) and uptake of uric acid. In cell culture, uric acid stimulates an increase in NADPH oxidase activity and ROS production in mature adipocytes but not in preadipocytes. The stimulation of NADPH oxidase-dependent ROS by uric acid resulted in activation of MAP kinases p38 and ERK1/2, a decrease in nitric oxide bioavailability, and an increase in protein nitrosylation and lipid oxidation. Hyperuricemia induces redox-dependent signaling and oxidative stress in adipocytes. Since oxidative stress in the adipose tissue is a known cause of insulin resistance and cardiovascular disease, hyperuricemia-induced alterations in oxidative homeostasis in adipose tissue is thought to play a role in these derangements.

Elevated serum uric acid and ADMA levels are associated with an increased cardiovascular risk, but their combination does not improve risk prediction. The effects are not additive, possibly because uric acid may lie in the causal pathway by which ADMA concentrations are substantially elevated by native or oxidized LDL cholesterol. Thus, a spiraling effect may occur with high LDL levels causing increased ADMA levels, which in turn inhibit nitric oxide production. Nitric oxide is needed to promote vasodilation. The elimination of ADMA occurs through urine excretion and metabolism by the enzyme dimethylarginine dimethylaminohydrolase (DDAH). The role of homocysteine as a risk factor for cardiovascular disease is thought to be mediated by homocysteine's down-regulating DDAH. Polyphenol antioxidants in turn play a role in down-regulating homocysteine. All of these factors likely interrelate in causing concentrations of hsCRP and other cytokine biomarkers of inflammation to lag uric acid concentrations by 15 to 30 hours. Both uric acid and hsCRP metabolisms exhibit approximately first-order exponential dynamics with half-lives of roughly 19 hours in vivo in humans. For this reason, in some embodiments, it is reasonable to serially monitor uric acid and hsCRP levels at sampling rates not exceeding daily.

Generally, embodiments described herein may utilize time series forecasting to build a model representing the physiological variables and then use this model on the recent values of the time series to extrapolate past behavior into future information. Parametric methods for estimating probabilities from time series include logistic regression, Cox proportional hazards regression, conditional proportional hazards regression, Weibull regression, Poisson regression, ARMA, ARIMA, and ARFIMA regression, log-Pearson Type 3 distribution (3-parameter gamma) regression, Generalized Extreme Value regression, Fréchet regression, and log-logistic accelerated failure time Generalized Additive Models for Location, Scale and Shape (GAMLSS). Non-parametric methods include random survival forests and survival trees. Forecasting methods may include different techniques and models. Moving-averages techniques, for example, or random-walk and trend models, exponential smoothing, state-space modeling, vector autoregressive models, cointegrated and causal models, methods based on neural, fuzzy networks or data mining and rule-based techniques are typical methods used in time series forecasting.

Some embodiments described herein determine transfer entropy (TE), which provides a non-parametric measure of directed (time-asymmetric) information transfer between joint processes. For Gaussian vector autoregressive (VAR) processes, transfer entropy may be equivalent to Granger causality. Some embodiments described herein determine bivariate spectral coherence, which has not previously been applied to time series of biomarkers of oxidative metabolism or inflammation.

Accordingly, at step 210, measurements are received of blood or serum physiological variables, such as serum or blood high-sensitivity C-reactive protein (hsCRP) and uric acid. The measurement information may be received (or extracted) from a patient's EHR, and/or from a measurement device such as described in connection to FIG. 1, which may be operated by the patient, by a caregiver, or automatically. In some embodiments, method 200 may comprise an initial determination of which specific blood or serum variables to utilize. Some embodiments of method 200 may comprise censoring any variable or value or time point affected by error or measurement artifact. Moreover, as described above, in contrast to the conventional technologies, an advantage of embodiments of method 200 (and thus an improvement over the conventional approach), is that due to the specific steps of method 200 and the physiological variables utilized as inputs, it is no longer necessary to measure arterial anatomy by invasive or imaging modalities. Specifically, surrogate physiological variables that have a strong statistical association with cardiovascular ischemia are sufficient, when utilized in a specific process such as described in the embodiments of method 200.

At step 220, the measured of blood or serum physiological variable values may be appended to a respective time series representing measurement values of the variables at corresponding date-time stamps. Some embodiments utilize a single time series comprising a plurality of measurements for each entry of the time series. Similarly, a separate time series may be utilized for each measured variable. This for a pair of measured variables, such as uric acid and serum or blood high-sensitivity C-reactive protein, two time series are determined. Accordingly, some embodiments of step 210 and 220 may comprise collecting serial quantitative measurements of at least two physicochemical properties of the blood or serum of a patient from one or a plurality of inputs. Some embodiments of step 210 or 220 may further comprise censoring any variable value or time point affected by effort or measurement artifact, such as a particular measurement value that is nonsensical (e.g., one that is orders of magnitude different than the others or one that has a value that is not humanly possible).

At step 230, a set of time series measurements comprising more recent measurements may be extracted or determined from the time series, and at step 235 it may be determined whether the time series is of sufficient length. (In other words, have a sufficient number of bivariate measurement pairs been acquired in step 210.) In general, a sufficient length may be any number of predetermined values (e.g., "N≥M" at step 235) that produces a reliable amplitude spectrum, as described below. One example of a sufficient length for uric acid values and hsCRP values is 32 values for each. In some cases, these values may be measured every other week. If not, then method 200 proceeds to step 280 to wait a number of T hours before receiving an additional measurement of the blood or serum variable values of the patent. In some embodiments, T is not less than 23 hours, such that measurements are not taken or received approximately less than once per day and may be received about daily, every other day or every several days, weekly, monthly, bi-annually, or the like. In some embodiments, T may be 12 or approximately one half of a day.

Next at step 245 a determination is made regarding whether the extracted or recent time series measurement values have constant values. If so, then method 200 proceeds to step 280 to wait a number of T hours before receiving an additional measurement of the blood or serum variable values of the patent. The specific method utilized by the embodiment of method 200 provides more accurate results where the values of the time series are not constant. Once it has been determined that the recent or extracted time series is of sufficient length and does not have only constant values, method 200 proceeds to step 250 where the time series is utilized to determine log returns. The time series may further be detrended and demeaned, in some embodiments.

Figure 3B:
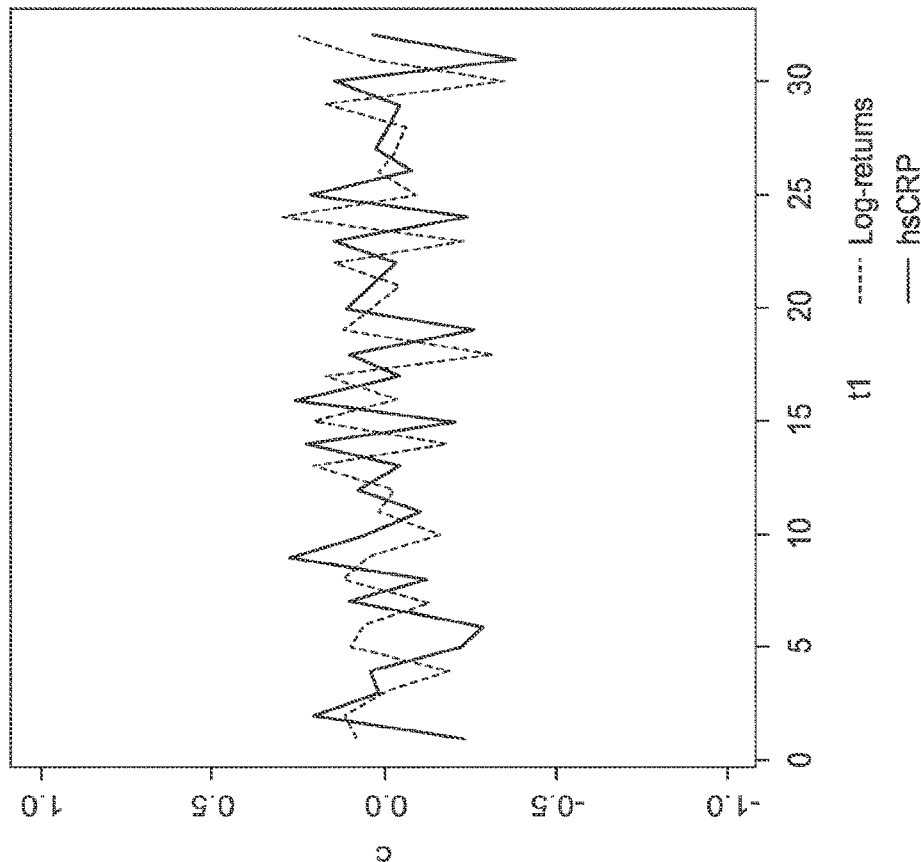
FIGS. 3A and 3B depict examples of log-return time series of uric acid and hsCRP for a healthy patient and a patient having acute coronary syndromes (ACS), in accordance with an example embodiment of the present disclosure actually reduced to practice.
Figure 3A:
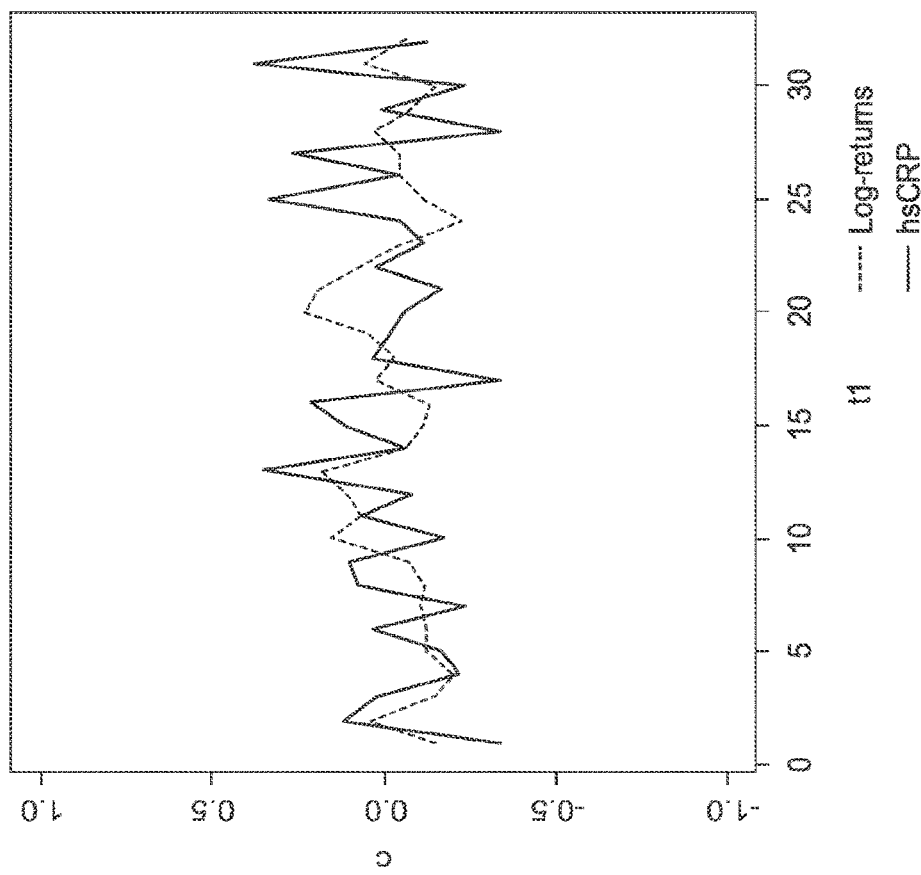

In particular, step 250 may comprise constructing a log-return time series from each raw time series of the physiological variable measurements received in step 210. From these calculations, a transfer entropy and spectral coherence may be determined. In some embodiments, step 250 comprises determining a frequency spectrum from said time series, by Fourier Transform or Wavelet Transform or other appropriate means, determining a transfer entropy of the bivariate time series or spectrum, and/or determining the spectral coherence of said bivariate time series or spectrum. Examples of log-return time series as determined from step 250 (from raw values of the physiological variables received in step 210) are shown in FIGS. 3A and 3B for a healthy control and ACS patient, respectively. Examples of spectral coherence determined from the log-return time series shown in FIGS. 3A and 3B (for a healthy control and ACS patient, respectively) are illustratively depicted in FIGS. 4A and 4B.

At step 260, the transfer entropy and spectral coherence then may be combined to generate a composite index representing an ischemic event risk forecast. In some embodiments, step 260 comprises combining the numeric values of transfer entropy and spectral coherence by thresholding, Boolean logical operations, weighted-sum, or similar means as may be known to those practiced in the art. An example embodiment of method 200, and in particular, steps 250 and 260, is provided in FIGS. 6A-6I, which depict an example computer program routine for generating a forecast of a cardiovascular ischemic event, such as an occurrence or recurrence, over a future time interval for a patient, evaluating the forecast, and based on the evaluation, implementing one or more response actions based on the generated forecast.

At step 265, the generated forecast may be evaluated against a threshold to determine whether one or more actions should be invoked because the determined likelihood of an ischemic event occurring is sufficiently high. In some embodiment, the threshold may be pre-determined, such as by a clinician, may be determined based in part on the particular physiological variables received in step 210 or based in part on other physiological parameters associated with the patient, such as the patient's sex, demographic, weight, previous occurrences of an ischemic event, presence of other conditions such as diabetes, hypertension, high blood pressure, etc., or the threshold may be dynamic or adaptive based on the patient and/or previous forecasts generated for the patient. In an embodiment, the threshold is 0.5 or represents a value corresponding to more than fifty percent likely that an ischemic event will occur.

At step 270, if it the generated forecast satisfies the threshold (i.e., if the forecast is outside the control limits indicating a likelihood of an ischemic event occurring over a future time interval, then invoke one or more actions. In particular, based on the generated forecast and/or score, one or more actions may be carried out automatically or may be recommended, as described herein. For example, the decision support tool may emit an alert to a caregiver via a decision support application 140, display a warning on a graphical user interface (such as user/clinician interface 142), generate a recommendation regarding the patient's disposition or care, or other action as described herein. In an embodiment, the decision support tool further determines whether the patient requires intensified monitoring or intervention, or may provide specific recommendations of care or may automatically schedule intervention by caregivers, consultations by specific caregivers, other healthcare resources (such as diagnostics or orders), or additional or modified care. In some embodiments, an application and graphical user interface are provided for displaying information related to the one or more actions and/or displaying aspects of the patient's condition based on the resulting determinations provided from method 200.

At step 275, method 200 may continue or end. In some embodiments, method 200 continues so that additional physiological variables are measured and received and a new forecast is generated. In some embodiments, method

200 may repeat continuously, periodically, occasionally, as needed, or when new respiratory information data becomes available. In particular, method 200 may be repeated as needed or if desired after a passage of time, such as every 12 hours, 24 hours, every other day, weekly, monthly, biannually, or the like, or may be repeated occasionally or as needed.

Example Reduction to Practice

With reference now to FIGS. 3A-7 and continuing reference to FIGS. 1A and 2, an example embodiment actually reduced to practice is described. This example reduced to practice was implemented using a server cluster (computer system 120) running the Linux operating system (operating system 129), the open-source statistical software package R, and the R modules mvLSW, seewave, and TransferEntropy.

A prospective research protocol was prepared entailing 32 days of daily measurements of blood uric acid (obtained using measurement device 141 comprising a Nesco NW-01 MultiCheck® hand-held instrument with Bluetooth data-transfer capability) and hsCRP (determined using measurement device 141 comprising a VITROS 5-FS® Chemistry System). Eight-minute hsCRP assay used 16 μL of blood from a finger prick and provided an analytical range of 0.001-100 mg/L with a lower detection limit of 0.06 (0.19) μg/L. The accuracy and precision of the assay were determined with coefficients of variation (CVs) of 2.3% (intra-assay) and 8.2% (inter-assay), recoveries of 95.4-103.1%, and linearity within 1%. The 20-second uric acid assay uses 4 μL of blood from a finger prick and provides an analytical range of 2.1-14.5 mg/dL. The CV was 2.9% (intra-assay) and 5.6% (inter-assay). Nineteen participants (6 having a history of ACS or AMI; 13 having no risk factors or ischemic event history) were recruited, informed, and consented for this example embodiment actually reduced to practice.

The ACS patients enrolled all received coronary angiography. According to the results of a coronary angiogram and the Gensini scores reflecting the severity of coronary artery disease, study subjects were divided into three groups: (i) mild severity group with scores below 50 (n=2); (ii) medium severity group with scores between 50 to 100 (n=2); and (iii) high severity group with scores greater than 100 scores (n=2). All patients met the ACS diagnostic criteria formulated by the American College of Cardiology/American Heart Association (ACC/AHA) in 2007. Exclusion criteria were as follows: (i) patients with other known heart diseases; (ii) patients with heart failure; (iii) patients with and liver dysfunction (AST, ALT, LDH, or alkaline phosphatase >2×ULN); (iv) patients with kidney function abnormality (creatinine >1.3 mg/dL); (v) patients with acute or chronic concurrent infection, hematologic disease, malignant tumors, rheumatism connective tissues and other immune system diseases; (vi) patients with recent surgery within the prior 60 days; (vii) patients with previous PCI angioplasty or stenting history; (viii) patients with diabetes mellitus or other endocrine diseases; (ix) patients with known cerebrovascular disease; and (x) patients with known symptomatic peripheral vascular disease.

Figure 4B:
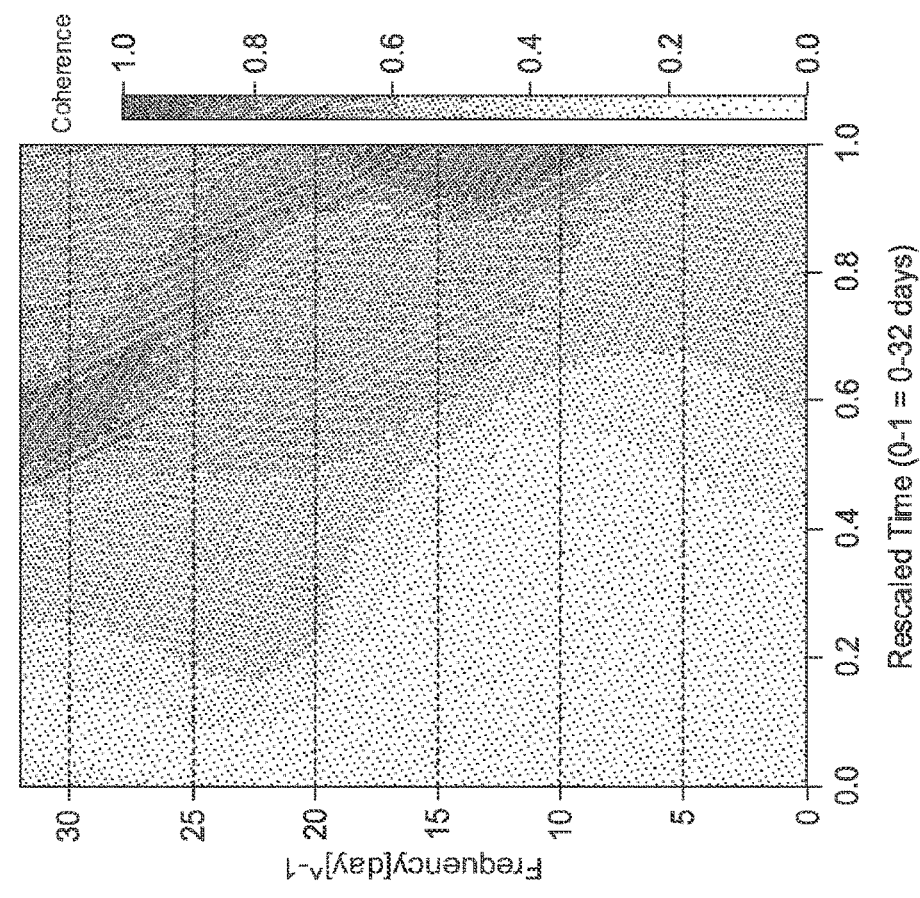
FIGS. 4A and 4B depict examples of spectrum coherence determinations from the time series of uric acid and hsCRP depicted in FIGS. 3A and 3B, in accordance with an example embodiment of the present disclosure actually reduced to practice.
Figure 4A:
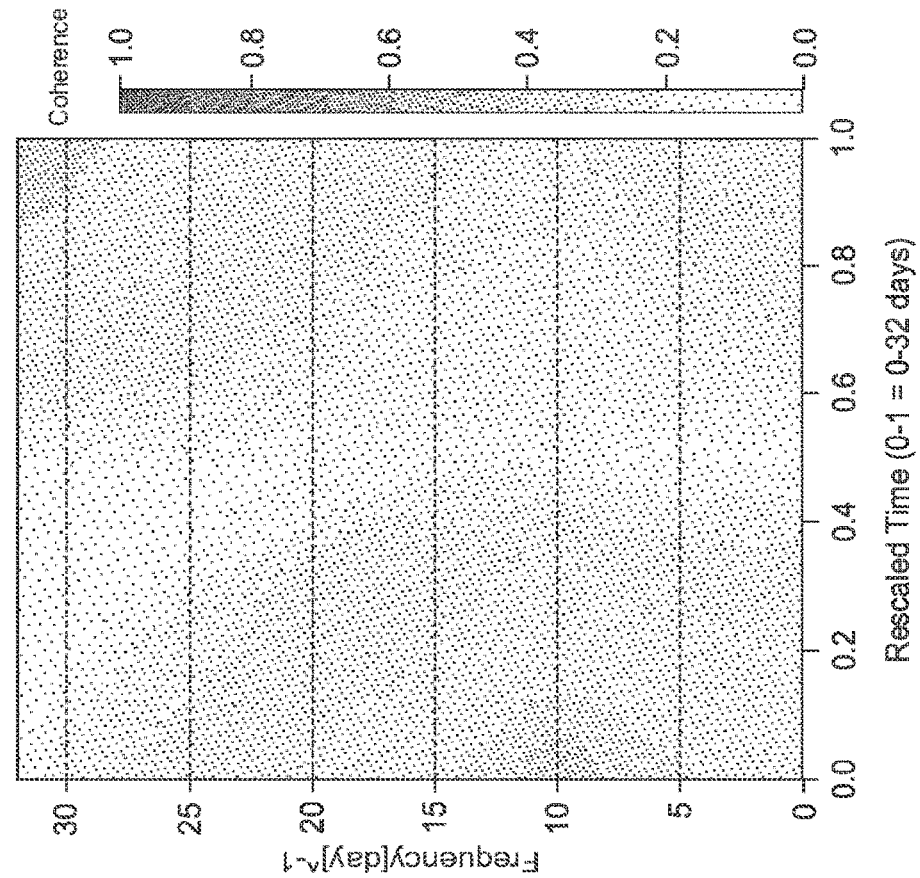
Figures 5A, 5B:
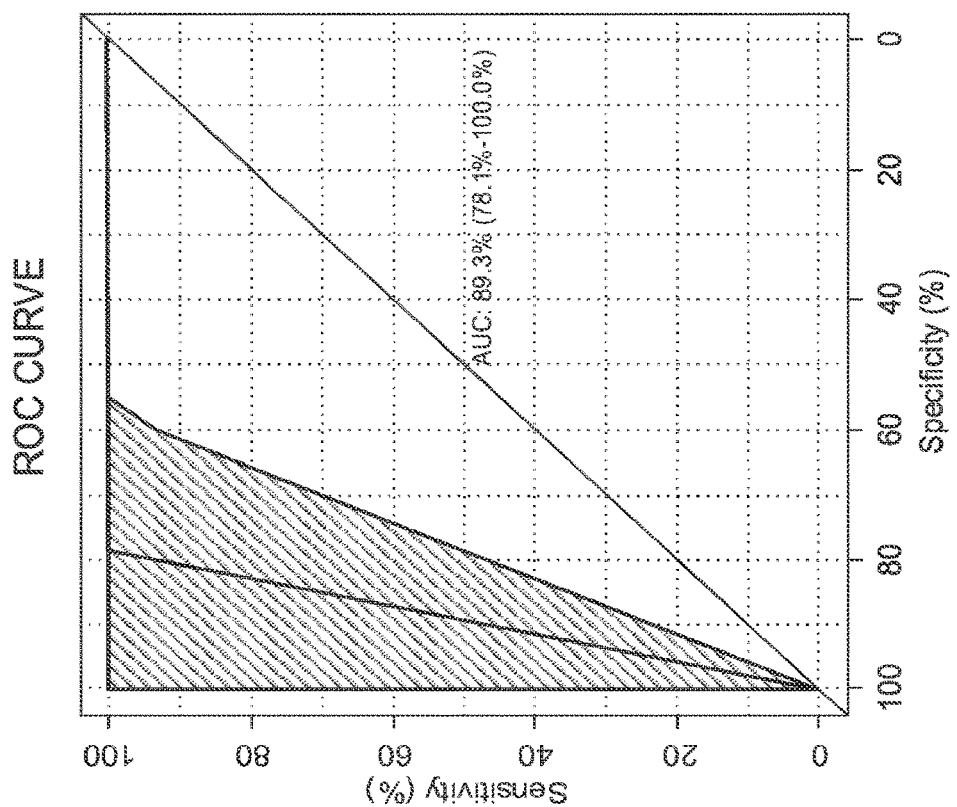
FIGS. 5A and 5B depict statistical performance of an example embodiment of the present disclosure actually reduced to practice, including a receiver operating characteristic (ROC) curve and table of statistical performance metrics indicating an improvement over the conventional technologies.

FIGS. 3B and 4B shows an example of an actual CAD patient's uric acid and hsCRP time series over the course of four weeks, where spectrum analysis calculations are performed. FIGS. 3A and 4A show similar information for healthy control patient. FIGS. 5A and 5B depict statistical performance of this example embodiment actually reduced to practice, including a receiver operating characteristic (ROC) curve (FIG. 5A) and table of statistical performance metrics (FIG. 5B) indicating an improvement over the conventional technologies. In particular, the ROC curve depicted in FIG. 5A represents a computation of exemplary 2-year forecasts for ischemic event (ACS or AMI) occurrence. As is known to those practiced in the art, the area under the ROC curve is a standard means of quantitatively assessing a classifier model's discrimination, the degree to which the model is able to accurately categorize cases into one or the other of two classes or categories—in this instance, "will experience an ischemic coronary event within 2 years" vs. "no event within 2 years." FIG. 7 illustratively provides an example embodiment of a computer program routine for generating the ROC curve shown in FIG. 5A.

Many different arrangements of the various components depicted, as well as components not shown, are possible without departing from the spirit and scope of the present technology. Embodiments of the present technology have been described with the intent to be illustrative rather than restrictive. Alternative embodiments will become apparent to those skilled in the art that do not depart from its scope. A skilled artisan may develop alternative means of implementing the aforementioned improvements without departing from the scope of the present technology. Additional example embodiments include the following:

Embodiment 1: A decision support tool for treating a cardiovascular condition, comprising: a computer processor; computer memory storing computer-readable instructions that when executed by the computer processor perform operations comprising: receiving blood information comprising a series of measurements of blood or serum physiological variables for the patient; determining one or more raw time series from the measurement values for each of the physiological variables represented in the blood information; determining a log-return time series from each of the one or more raw time series thereby forming one or more log-return time series; utilizing the one or more log-return time series, determining a transfer entropy and spectral coherence; determining a composite index by combining the transfer entropy and spectral coherence, the composite index representing an ischemic event risk forecast over a future time interval; determining that the composite index satisfies a threshold; and in response to determining that the composite index satisfies a threshold, determining to initiate an intervening action.

Embodiment 2: Embodiment 1, wherein the blood or serum physiological variables comprise high-sensitivity C-reactive protein (hsCRP) and uric acid.

Embodiment 3: Any of Embodiments 1-2, wherein determining the log time series further comprises detrending and demeaning the one or more time series.

Embodiment 4: Any of Embodiments 1-3, wherein each measurement in the series of measurements of blood or serum physiological variables, after the first measurement, occurs at least twenty-three hours from the previous measurement.

Embodiment 5: Any of Embodiments 1-4, wherein the blood or serum physiological variables comprise high-sensitivity C-reactive protein (hsCRP) and uric acid, and wherein each measurement for uric acid is measured approximately daily and each measurement of hsCRP is measured approximately weekly.

Embodiment 6: Any of Embodiments 1-5, wherein future time interval comprises one of up to six months, up to one year, between one and five years, or between one and ten years.

Embodiment 7: Any of Embodiments 1-6, wherein the threshold is 0.5.

Embodiment 8: Any of Embodiments 1-7, wherein the intervening action comprises issuing an alert.

Embodiment 9: Any of Embodiments 1-8, wherein the spectral coherence is determined using Fourier Transform or Wavelet Transform.

Embodiment 10: A method for monitoring at least one human patient, comprising: collecting serial quantitative measurements of at least two physicochemical properties of the blood or serum of a patient from one or a plurality of inputs thereby forming a raw time series for each physicochemical property; constructing a log-return time series from each raw time series; demeaning and detrending each log-return time series thereby forming a set of log-return time series; determining a frequency spectrum from the set of log-return time series, by Fourier Transform or Wavelet Transform; determining a transfer entropy of the set of log-return time series; determining the spectral coherence of the determined frequency spectrum; determining a composite index of ischemic event risk by combining the spectral coherence and transfer entropy; and determining a forecast for the likelihood of ischemic cardiovascular events, based on the composite index.

Embodiment 11: Embodiment 10, wherein the at least two physicochemical properties comprise high-sensitivity C-reactive protein and uric acid, and wherein the set of log-return time series comprise bivariate time series.

Embodiment 12: Any of Embodiments 10-11, wherein the forecast comprises a risk of ischemic cardiovascular event risk score at one or a plurality of future time points.

Embodiment 13: Any of Embodiments 10-12, wherein the transfer entropy determined from uric acid to hsCRP>+0.3 and bivariate spectral coherence >0.4 jointly denote increased risk of cardiovascular ischemic event(s) within a multi-year time horizon.

Embodiment 14: Any of Embodiments 10-13, wherein determining a composite index of ischemic event risk by combining the spectral coherence and transfer entropy comprises combining the numerical values of spectral coherence and transfer entropy by thresholding, Boolean logical operations, or weighted-sum.

Embodiment 15: Any of Embodiments 10-14, wherein determining a composite index of ischemic event risk by combining the spectral coherence and transfer entropy further comprises determining an arithmetic mean or the median of the combined numerical values of spectral coherence and transfer entropy.

Embodiment 16: Any of Embodiments 10-15, wherein determining the combined values are determined by a linear combination of the numerical values.

Embodiment 17: Any of Embodiments 10-16, wherein determining the combined values are determined by using the minimum or the maximum numerical values.

Embodiment 18: Any of Embodiments 10-17, wherein serial quantitative measurements are performed with a frequency between 1 and 14 times per fortnight.

Embodiment 19: Any of Embodiments 10-18, wherein serial quantitative measurements are performed between 1 and 7 times per week.

Embodiment 20: Any of Embodiments 10-19, further comprising generating a reporting message based on the forecast, the reporting message including a graphical display or time-oriented plot of the trend of multiple serial determinations of the ischemic event risk.

Embodiment 21: Any of Embodiments 10-20, wherein the forecasting time horizon is at least one year into the future.

Embodiment 22: Any of Embodiments 10-21, wherein the forecasting time horizon is between one and five years into the future or between one and ten years into the future.

Embodiment 23: Any of Embodiments 10-22, wherein the at least one human patient has hsCRP values in the upper tertile.

Embodiment 24: Any of Embodiments 10-23, wherein the set of log-return time series comprise bivariate time series and wherein the two physicochemical properties are processed using mixed-frequency methods.

Embodiment 25: Any of Embodiments 10-24, wherein the two physicochemical properties comprise high-sensitivity C-reactive protein and uric acid, and wherein the measurements of each physicochemical property is different from the other property.

Embodiment 26: Any of Embodiments 10-25, wherein the measurements of uric acid is daily and wherein the measurement of hsCRP is weekly.

Embodiment 27: A method for assessing a patient, the method comprising: a) receiving date-time stamped medical data about the patient from one or more data sources, wherein the medical data comprises data points from a plurality of times; b) computing from a plurality of at least 32 time points the patient's predicted risk of occurrence or recurrence of ischemic cardiovascular event(s) based on the data from those time points; c) forecasting into the future with a time horizon during which the likelihood of occurrence or recurrence of ischemic cardiovascular event(s) is estimated; and d) emitting a report or electronic message to a human decision-maker regarding said predicted risk.

Embodiment 28: Embodiment 27, wherein serial monitoring and risk calculations, forecasting, or trend analysis are initiated some weeks after the first occurrence of ischemic cardiovascular event.

Embodiment 29: Any of Embodiments 26-28, wherein the patient has hsCRP values in the upper tertile.

Embodiment 30: Any of Embodiments 26-29, wherein computing from a plurality of at least 32 time points the patient's predicted risk of occurrence or recurrence of ischemic cardiovascular event(s) based on the data from those time points includes determining a log-return time series from the 32 time points, and utilizing the one or more log-return time series to determine a transfer entropy and spectral coherence.

It will be understood that certain features and subcombinations are of utility and may be employed without reference to other features and subcombinations and are contemplated within the scope of the claims. Not all steps listed in the various figures need be carried out in the specific order described. Accordingly, the scope of the technology is intended to be limited only by the following claims.

What is claimed is:

1. An electronic medical record (EMR) system for determining a cardiovascular ischemic event, the EMR system associated with a patient and comprising one or more processors configured to cause a plurality of operations, the operations comprising:

collecting via a measurement device and recording, in a digital memory, measurement data comprising values for one or both of select blood variables associated with the patient and select serum variables associated with the patient, the values comprising a series of C-reactive protein (CRP) measurements and a series of uric acid measurements;

in response to detecting a set of constant values in the measurement data, abstaining from processing the measurement data for an interval of time;

initiating, after passage of the interval of time, by the EMR system:
identifying CRP and uric acid log-return time series from the series of CRP measurements and uric acid measurements, respectively;
utilizing the CRP log-return time series and the uric acid log-return time series to determine a transfer energy and a spectral coherence;
generating a composite index for an ischemic event based on the transfer energy and based further on the spectral coherence;
evaluating the composite index against a threshold associated with CRP and uric acid physiological parameters;
based on evaluating the composite index against the threshold, automatically diagnosing cardiovascular ischemia, by an EMR, without arterial anatomy being measured by invasive or imaging modalities; and
determining a particular treatment, for the patient based on the automatic diagnosing of cardiovascular ischemia to administer to the patient to treat the cardiovascular ischemia of the patient.

2. The system of claim 1, the operations further comprising:
measuring to obtain an CRP value and a uric acid value associated with the patient;
appending the CRP value to the series of CRP measurements as a most recent CRP value; and
appending the uric acid value to the series of uric acid measurements as a most recent uric acid value.

3. The system of claim 1, the operations further comprising:
determining the series of CRP measurements includes at least a predetermined number of CRP values;
determining the series of uric acid measurements includes at least a predetermined number of uric acid measurements;
removing from the series of CRP measurements an CRP measurement based on determining that the CRP measurement is a non-possible CRP measurement or deviates from the series of CRP measurements by a predetermined order of CRP magnitude, wherein the CRP measurement is removed prior to determining the series of CRP measurements includes the predetermined number of CRP values; and
removing from the series of uric acid measurements a uric acid measurement based on determining that the uric acid measurement is a non-possible uric acid measurement or deviates from the series of uric acid measurements by a predetermined order of uric acid magnitude, wherein the uric acid measurement is removed prior to determining the series of uric acid measurements includes the predetermined number of uric acid values.

4. The system of claim 1, the operations further comprising:
determining whether the series of CRP measurements includes constant values;
determining whether the series of uric acid measurements includes constant values; and
based on determining that either the series of CRP measurements includes constant values or the series of uric acid measurements includes constant values, receiving a value of an additional CRP measurement or an additional uric acid measurement after a predetermined length of time.

5. The system of claim 1, the operations further comprising detrending and demeaning the CRP log-return time series and the uric acid log-return time series.

6. The system of claim 1, wherein at least one of a Fourier Transform or a Wavelet Transform are utilized to determine the transfer energy and the spectral coherence.

7. The system of claim 1, wherein the threshold is further determined based on physiological parameters.

8. The system of claim 1, wherein the CRP log-return time series and the uric acid log-return time series each comprise a bivariate time series.

9. A computer-implemented method for determining, at an electronic medical record (EMR) associated with a patient, a cardiovascular ischemic event, the computer-implemented method comprising:
collecting via a measurement device and recording, in a digital memory, measurement data comprising values for one or both of select blood variables associated with the patient and select serum variables associated with the patient, the values comprising a series of C-reactive protein (CRP) measurements and a series of uric acid measurements;
in response to detecting a set of constant values in the measurement data, abstaining from processing the measurement data for an interval of time;
initiating, after passage of the interval of time, by the EMR:
identifying CRP and uric acid log-return time series from the series of CRP measurements and uric acid measurements, respectively;
utilizing the CRP log-return time series and the uric acid log-return time series to determine a transfer energy and a spectral coherence;
generating a composite index for an ischemic event based on the transfer energy and based further on the spectral coherence;
evaluating the composite index against a threshold associated with CRP and uric acid physiological parameters;
based on evaluating the composite index against the threshold, automatically diagnosing cardiovascular ischemia, by the EMR, without arterial anatomy being measured by invasive or imaging modalities; and
determining a particular treatment, for the patient based on the automatic diagnosing of cardiovascular ischemia to administer to the patient to treat the cardiovascular ischemia of the patient.

10. The method of claim 9, wherein the series of CRP measurements includes at least a predetermined number of CRP values, and determining the series of uric acid measurements includes at least a predetermined number of uric acid measurements.

11. The method of claim 9, further comprising:
removing from the series of CRP measurements an CRP measurement based on determining that the CRP measurement: is a non-possible CRP measurement or deviates from the series of CRP measurements by a predetermined order of CRP magnitude; and
removing from the series of uric acid measurements a uric acid measurement based on determining that the uric acid measurement: is a non-possible uric acid measurement or deviates from the series of uric acid measurements by a predetermined order of uric acid magnitude.

12. The method of claim 9, further comprising:
determining whether the series of CRP measurements includes constant values;

determining whether the series of uric acid measurements includes constant values; and based on determining that either the series of CRP measurements includes constant values or that the series of uric acid measurements includes constant values, receiving a value of an additional CRP measurement or an additional uric acid measurement after a predetermined length of time.

13. The method of claim 9, further comprising initiating an intervention action for the patient based on evaluating the composite index against the threshold, wherein the intervention action comprises providing a medical order to modify a treatment for the ischemic event associated with the patient.

14. The method of claim 9, wherein at least one of a Fourier Transform and a Wavelet Transform are utilized to determine the transfer energy and the spectral coherence.

15. One or more non-transitory media having instructions that, when executed by one or more processors, cause a plurality of operations that enable an electronic medical record (EMR) associated with a patient to determine a cardiovascular ischemic event, the operations comprising:

collecting via a measurement device and recording, in a digital memory, measurement data comprising values for one or both of select blood variables associated with the patient and select serum variables associated with the patient, the values comprising a series of C-reactive protein (hsCRP) (CRP) measurements and a series of uric acid measurements;

in response to detecting a set of constant values in the measurement data, abstaining from processing the measurement data for an interval of time;

initiating, after passage of the interval of time, by the EMR:

identifying CRP and uric acid log-return time series from the series of CRP measurements and uric acid measurements, respectively;

utilizing the CRP log-return time series and the uric acid log-return time series to determine a transfer energy and a spectral coherence;

generating a composite index based on the transfer energy and based further on the spectral coherence;

evaluating the composite index against a threshold associated with CRP and uric acid physiological parameters;

based on evaluating the composite index against the threshold, automatically diagnosing cardiovascular ischemia, by the EMR, without arterial anatomy being measured by invasive or imaging modalities; and determining a particular treatment, for the patient based on the automatic diagnosing of cardiovascular ischemia to administer to the patient to treat the cardiovascular ischemia of the patient.

16. The one or more non-transitory media of claim 15, further comprising determining the series of CRP measurements includes at least thirty-two CRP values, and determining the series of uric acid measurements includes at least thirty-two uric acid measurements.

17. The one or more non-transitory media of claim 15, further comprising:

removing from the series of CRP measurements an CRP measurement based on determining that the CRP measurement is a non-possible CRP measurement or deviates from the series of CRP measurements by a predetermined order of CRP magnitude; and removing from the series of uric acid measurements a uric acid measurement based on determining that the uric acid measurement is a non-possible uric acid measurement or deviates from the series of uric acid measurements by a predetermined order of uric acid magnitude.

18. The one or more non-transitory media of claim 15, further comprising:

determining whether the series of CRP measurements includes constant values;

determining whether the series of uric acid measurements includes constant values; and based on determining that either the series of CRP measurements includes constant values or the series of uric acid measurements includes constant values, receiving a value of an additional CRP measurement or an additional uric acid measurement after a predetermined length of time.

19. The one or more non-transitory media of claim 15, further comprising detrending and demeaning the CRP log-return time series and the uric acid log-return time series.

20. The one or more non-transitory media of claim 15, further comprising providing a notification to modify a treatment for preventing a potential cardiac event.

\* \* \* \* \*